United States Patent
Wang et al.

(10) Patent No.: US 9,842,151 B2
(45) Date of Patent: Dec. 12, 2017

(54) SYSTEM AND METHOD FOR UPLOADING AND MANAGEMENT OF CONTRACT-RESEARCH-ORGANIZATION DATA TO A SPONSOR COMPANY'S ELECTRONIC LABORATORY NOTEBOOK

(71) Applicant: PerkinElmer Informatics, Inc., Waltham, MA (US)

(72) Inventors: Yong Wang, Westborough, MA (US); Christopher P. Strassel, East Bridgewater, MA (US); Kathleen R. Moxham, Hopkinton, MA (US); Mark P. Jackson, Saul Gloucester (GB); Churl Oh, Concord, MA (US)

(73) Assignee: PerkinElmer Informatics, Inc., Waltham, MA (US)

( * ) Notice: Subject to any disclaimer, the term of this patent is extended or adjusted under 35 U.S.C. 154(b) by 107 days.

(21) Appl. No.: 14/206,960

(22) Filed: Mar. 12, 2014

(65) Prior Publication Data
US 2015/0169717 A1    Jun. 18, 2015

Related U.S. Application Data

(60) Provisional application No. 61/916,110, filed on Dec. 13, 2013.

(51) Int. Cl.
*G06F 17/30* (2006.01)
*G06F 11/14* (2006.01)
(Continued)

(52) U.S. Cl.
CPC .... *G06F 17/30575* (2013.01); *G06F 11/1453* (2013.01); *G06F 19/327* (2013.01);
(Continued)

(58) Field of Classification Search
CPC .................................................. G06F 17/30575
(Continued)

(56) References Cited

U.S. PATENT DOCUMENTS

| 7,054,823 B1 | 5/2006 | Briegs et al. |
| 2003/0055830 A1 | 3/2003 | Gutierrez-Rivas et al. |

(Continued)

OTHER PUBLICATIONS

International Search Report, PCT/US2014/024725 dated Jul. 25, 2014.

(Continued)

*Primary Examiner* — Thu-Nguyet Le
(74) *Attorney, Agent, or Firm* — Choate, Hall & Stewart LLP; William R. Haulbrook; Ronen Adato

(57) ABSTRACT

The present disclosure provides a system and method for comprehensive data synchronization management between a sponsor-company's central electronic-laboratory-notebook system and either multiple contract-research-organizations or research sites. The system features a data loader server that can be deployed on-premise or in the cloud and allows scheduling of synchronization jobs of electronic-laboratory-notebook. The data loader software communicates to the contract research organization and the sponsor company's electronic laboratory notebook and executes scheduled or on-demand jobs. The data loader software may synchronized subsequent update of the data and may automatically delete the data from the contract research organization's site once a given transfer is complete. In some implementations, the method and system is configured for automation, scalability, and high-performance operations that focused on efficiency, security, configurability, and privacy/intellectual property protection.

21 Claims, 17 Drawing Sheets

(51) Int. Cl.
*H04L 29/06* (2006.01)
*G06F 19/00* (2011.01)
*G06F 21/62* (2013.01)
*G06Q 50/24* (2012.01)

(52) U.S. Cl.
CPC ........ *H04L 63/0428* (2013.01); *G06F 19/366* (2013.01); *G06F 21/6245* (2013.01); *G06Q 50/24* (2013.01); *H04L 63/0272* (2013.01)

(58) Field of Classification Search
USPC .................................................. 707/620, 656
See application file for complete search history.

(56) References Cited

U.S. PATENT DOCUMENTS

| | | | | |
|---|---|---|---|---|
| 2004/0243439 | A1* | 12/2004 | Huggard | G06F 19/363 705/2 |
| 2005/0182657 | A1 | 8/2005 | Abraham-Fuchs et al. | |
| 2006/0224421 | A1* | 10/2006 | St. Ores | A61B 5/0031 705/4 |
| 2007/0067711 | A1 | 3/2007 | Woodall et al. | |
| 2008/0256128 | A1 | 10/2008 | Pierce et al. | |
| 2010/0228699 | A1* | 9/2010 | Webber | G06F 17/30557 707/622 |
| 2013/0144790 | A1 | 6/2013 | Clements | |
| 2015/0081718 | A1 | 3/2015 | Schmidt | |

OTHER PUBLICATIONS

Cassells, S. et al., Case Report Tabulation Data Definition Specification (define.xml), CDISC, 45 pages (2003-2004).
CDISC Submission Data Standards Team, Study Data Tabulation Model, Version 1.4, CDISC, 40 pages (2013).
CDISC, Specification for the Operational Data Model (ODM), 54 pages, (2006) retieved on Oct. 21, 2016 <http://www.cdisc.org/system/files/all/generic/application/octet-stream/odm1_3_0_final.htm>.
CDISC, Study Data Tabulation Model (SDTM), Standard Overview, 3 pages, (2016) retrieved on Oct. 21, 2016, <http://www.cdisc.org/standards/foundational/sdtm>.
Graebner, R. W., Practical methods for Creating CDISC SDTM Domain Data Sets from Existing Data, SAS Global Forum, Pharma, Life Science and Healthcare, 11 pages (2008).
Hangfire, Job Control Documentation, 5 pages, retrieved on Oct. 21, 2016, <http://docs.hangfire.io/en/latest/>.
Iavindrasana, J. et al., Clinical Data Mining: A Review, IMIA and Schattauer GmbH, 13 pages (2009).
Medidata Rave: Unified EDC & CDMS Solution | Medidata Solutions, 4 pages, retrieved Oct. 21, 2016 on <https://www.mdsol.com/en/what-we-do/data-capture/medidata-rave>.
Medidata, Capturing the Value of EDC, medidata, 19 pages (2013).
OHDSI, Data Standardization, OHDSI, 3 pages, retrieved Oct. 21, 2016 <http://www.ohdsi.org/data-standardization/>.
Oracle Health Sciences Inform, Oracle Inform Overview, 2 pages, retrieved from on Oct. 21, 2016<http://www.oracle.com/us/products/applications/health-sciences/e-clinical/inform/index.html>.
Oracle Health Sciences, Oracle Health Sciences Inform: Comprehensive Clinical Data Caputer and Management Cloud, Oracle, 12 pages (2015).
Rave Web Services, A Valid ODM 1.3 Transactional Document, 1 page, retrieved on Oct. 21, 2016, <http://rws-webhelp.s3.amazonaws.com/WebHelp_ENG/features/common/01_valid_odm_%20transactional_document.html#valid-odm-transactional-document <http://rws-webhelp.s3.amazonaws.com/WebHelp_ENG/features/common/01_valid_odm_%20transactional_document.html>.
Rave Web Services, A Vlaid ODM 1.3 Snapshot Document, 1 page, retrieved Oct. 21, 2016, <http://rws-webhelp.s3.amazonaws.com/WebHelp_ENG/features/common/02_valid_odm_%20snapshot_document.html#valid-odm-snapshot-document <http://rws-webhelp.s3.amazonaws.com/WebHelp_ENG/features/common/02_valid_odm_%20snapshot_document.html>.
Rave Web Services, Complex formats, 2 pages (2014), retrieved on Oct. 21, 2016, <http://rws-webhelp.s3.amazonaws.com/WebHelp_ENG/features/12_configurable_datasets/03_complex_rendering.html#cds-complex-rendering <http://rws-webhelp.s3.amazonaws.com/WebHelp_ENG/features/12_configurable_datasets/03_complex_rendering.html>.
Rave Web Services, ODM Schema, 3 pages (2014), retrieved on Oct. 21, 2016, <http://rws-webhelp.s3.amazonaws.com/WebHelp_ENG/features/common/03_odm_schema.html>.
Rave Web Services, Using ODM, 4 pages (2014), retrieved on Oct. 21, 2016, <http://rws-webhelp.s3.amazonaws.com/WebHelp_ENG/introduction/using_odm.html#vendor-extensions <http://rws-webhelp.s3.amazonaws.com/WebHelp_ENG/introduction/using_odm.html>.
SAS and Pharmaceutical Executive, Rethinking Clinical Trials Data Integration, SAS, 5 pages (2009).
SAS, Fact Sheet, Clinical Data Integration, 4 pages (2014).
SAS, SAS® Clinical Data Integration, 6 pages, retrieved on Oct. 21, 2016, <http://www.sas.com/en_ph/industry/life-sciences/clincial-data-integration.html>.
Sparks, I., rwslib Documentation, Release 1.1.5, Rave Web Services, 72 pages (2016).
Stuelpner, J. and Shostak, J., Confessions of a Clinical Programmer: Creating SDTM Domains with SAS®, SAS, 19 pages, (2011).
Torres-Reyna, O., Merge/Append using R, Data & Statistical Services, Princeton University, 14 pages (2011).
Who, Essential medicines and health products, Pharmacovigilance, 2 pages, retrieved on Oct. 21, 2016, <http://www.who.int/medicines/areas/quality_safety/safety_efficacy/pharmvigi/en/>.
Wikipedia, Data modeling, 8 pages, retrieved Oct. 21, 2016, <https://en.wikipedia.org/wiki/Data_modeling>.
Wikipedia, Join (SQL), Wikipedia, 14 pages (2016) [retrieved Jan. 3, 2017].

* cited by examiner

FIG. 5A

502 — form containing:
- Job Name (504)
- Job Type (506)
- E-Notebook Server
- Owner (508)
- Collection Type — 518
- State (510)
- Modified Date [Is AnyTime] — 520
- 512b ☐ Schedule Job | 512A ☐ Run Now | ☐ Notify Me | 512C ☐ Active
- 512
- Start Date & Time — 514
- Repeat Every [ ] [Days] — 516
- 517 [Preview Collections] [Schedule Jobs]

FIG. 5B

525 — Job List (528)

| Name | E-Notebook Server [All] | Created by [All] |
|---|---|---|
| IMP JB BB 3114 | Pharma ELN_PKI_secured  530 | bibin  532 |
| Chris's job | Edit | Schedule Import ...loader | |
| EXP JB BB 3108 | CRO_ELN-Calphine_Secured | bibin |

526 — [Add New Job]

| | | 532 |
|---|---|---|
| EXP Job BB 1 | Edit | Delete | Schedule Import | |
| EXP Job CK1 | CRO_ELN_Secured | baiju |

526 — 530

SYSTEM AND METHOD FOR UPLOADING AND MANAGEMENT OF CONTRACT-RESEARCH-ORGANIZATION DATA TO A SPONSOR COMPANY'S ELECTRONIC LABORATORY NOTEBOOK

PRIORITY

This application claims the benefit of U.S. Provisional Application No. 61/916,110, filed Dec. 13, 2013. This application is incorporated by reference herein in its entirety.

TECHNICAL FIELD

This disclosure relates generally to the management of data entered by multiple outside parties (e.g., contract research organizations) into an organization's Electronic Laboratory Notebook.

BACKGROUND

A contract research organization ("CRO") is an organization that provides support to the pharmaceutical, biotechnology, and medical device industries in the form of research services outsourced by one or more sponsor companies on a contract basis. Research services may include, for example, biopharmaceutical development, biologic assay development, commercialization, pre-clinical research, clinical research, clinical trials management, and pharma-covigilance, among others. Contract research organizations may also provide clinical-study and clinical-trial support for drugs and/or medical devices.

To conform to regulatory guidelines and policies on the handling of clinical data and to secure intellectual property ("IP") assets, sponsor companies typically mandate that the contract research organizations input their experimental data into the sponsor companies' central Electronic Laboratory Notebook ("ELN") system. An electronic laboratory notebook is generally a computing application that replaces paper laboratory notebooks used by scientists, engineers, and technicians to document research, experiments, and procedures performed in a laboratory. Entries into laboratory notebooks are often governed by guidelines and policies of a given organization and/or company.

Existing products for managing contract research organization's data often fail to account for the specific requirements of this service and, thus, do not adequately meet the need for security, privacy, performance, and consistency. For example, some existing products allow a contract-research-organization remote access to a sponsor companies' central electronic laboratory notebook database to input/update their data. This access is not only unnecessary to synchronize data between the various databases; it poses risk to security, theft, privacy, and industrial espionage. Additionally, because a given sponsor company's electronic laboratory notebook may have many users and notebook collections, having additional members from the contract research organization share the same resource may degrade the performance of such systems. Moreover, network latency and performance issues associated with live-update of the research data via remote operation may further generate unnecessary delays and inconvenience for the contract-research-organization members.

FIG. 1 is a prior art system for managing data between a contract-research-organization data and a sponsor company's electronic laboratory notebook. To upload or update a sponsor company's electronic laboratory notebook, a set of contract-research-organization researchers remotely login to an electronic laboratory notebook operating at the sponsor company and update the data via an E-Notebook client. The remote login may be made by way of a virtual private network ("VPN") using a virtualization server (for example, a Citrix server). The contract-research-organization researcher may update the electronic-laboratory-notebook entries manually and remotely. Analysts working for the sponsor company may then analyzed the research data. When accessed by a large number of users, such systems may provide slow performance to both the local and remote users.

Other existing systems allow a contract research organization to use an electronic-laboratory-notebook scheme of that of the sponsor company to create a project report in portable document format ("PDF") at the end of the project. This type of products may create inconsistent work-flow between the contract research organization and the sponsor company. Moreover, different formats after the import creates further inefficiencies in the data transfer and when searching for specific information within the data.

Other existing systems allow a contract research organization to connect to a hosted electronic-laboratory-notebook server and database, where the data is separated from the sponsor company's main electronic-laboratory-notebook database. The product may employ a merge function, such as "extract-transform-load" to incorporate the contract research organization data into the sponsor company's database. This type of products may result in a potentially inconsistent work flow between the contract research organization and different sponsors. Additionally, the electronic-laboratory-notebook data formats may be different among the databases resulting in an integration issues.

There exists a need for an approach to an electronic-laboratory-notebook system that provides high performance and secure global remote access for users with requisite privacy protection and consistency.

SUMMARY

In general overview, an intermediary party provides, to a contract research organization ("CRO") or a sponsor company, a computing application to securely collect and synchronize the CRO data with a sponsor company's database without access of the database by end-users of the contract research organization. Moreover, the computing application provides the CRO researchers with a low-latency electronic laboratory notebook ("E-Notebook") to log experimental data that conforms to the E-Notebook format of the sponsor E-Notebook system. The computing application provides a secure global transfer access of such data from the CRO E-notebook to a sponsor E-Notebook system.

In some implementations, the computing application comprehensively manages and synchronizes data between a sponsor company's central E-Notebook system and multiple E-Notebooks of CROs.

In some implementations, the computing application sets up a local E-Notebook system at a contract-research-organization site or in the cloud. To this end, the local E-Notebook or cloud E-Notebook does not interface with the sponsor company E-Notebook. In addition, an update of the CRO data would not be subjected to performance issues that may be caused by network latency associated with remotely working through a networked session. Moreover, because the CRO E-Notebook typically include less data than the sponsor company's E-Notebook, the users (for example, researchers) at the CRO preferably have a better response time using the local system, which services a smaller data set, than remotely accessing the sponsor's E-Notebook, which services a larger data sets. The sponsor's E-Notebook may be subjected to multiple remote data sources that further impede the response time of the system.

In some implementations, the system includes a data loader server that preferably deploys on-premise (for example, at a sponsor company's site) or in the cloud and allows scheduling of E-Notebook synchronization jobs, for example, by an administrator of the sponsor company. To this end, the data loader server may operate in a fully automated manner after the initial configuration, which may be configured using an easy-to-use Web-based graphical-user-interface. The data loader server communicates to a sponsor company's E-Notebook systems and may execute scheduled or on-demand jobs. In some implementations, the system is preferably configured to improve performance, scalability, security, intellectual property and privacy protection, and automation.

For example, to improve efficiency and automation, the system may facilitate the scheduling of different data synchronization activities by an administrator, for example, export, import, and delete activities, among others, with the CRO. The data loader may provide a Web interfaces for an administrator to perform the scheduling. Synchronization activities can be executed automatically, without requiring an administrator's or end-user's interaction. The scheduling Web interface may include one or more filters that allow an administrator to select a desired type of data in the CRO E-Notebook system data set. The data loader may send alerts and notifications to an administrator or end-user to inform them of successful updates and of errors and failed updates and, thus, allowing them to manage the data more efficiently and to respond to issues more quickly.

To facilitate scalability, the system supports multiple data loader servers in different geographic locations.

To improve security and IP/privacy protection, the system supports the use of encryption and user management technology to protect critical E-Notebook data both during-transit and at-rest. In using a separate E-Notebook system than the central sponsor E-Notebook system, the system prevents external sources (i.e., CRO) from having unnecessary access to the sponsor's critical data thereby addressing concerns from the sponsor companies about IP and privacy protection. The system also supports physical deletion of sensitive E-Notebook data from a CRO system after the data has been successfully synchronized to the central sponsor E-Notebook system, thereby providing a comprehensive IP protection for the sponsor company.

In some implementations, the system may include (i) a Data Loader (e.g., Windows) Web Service that centralizes management of user interfaces and network connections among Data Loader server, web browser, and E-Notebook systems; (ii) a Data Loader Job Scheduler that allows one or more users to schedule and manage different synchronization jobs; (iii) a Data Loader Job Runner that can execute different synchronization jobs; (iv) a Data Loader Runner (e.g., Windows) Service that can initiate jobs based on scheduled activities; and/or (v) a Data Loader Cross-Cutting Concern Manager that can handle different cross-cutting concerns, such as security, notifications and alerts, and the like.

In some embodiments, the system may use, for data storage on the Data Loader server, (i) a commercial enterprise software database that can store different types of data including scheduling, Data Loader user management, and synchronization metadata, and the like; and (ii) a staging area that is located on the hard drive of the Data Loader Server and can store raw E-Notebook exported data files.

Applications for the systems and methods described herein are not limited to the aforementioned examples, but may be deployed in any number of contexts, as would be understood by one of ordinary skill in the art. Contents of the background are not to be considered as an admission of the contents as prior art.

In one aspect, the present disclosure describes a method of secure upload and management of data from one or more contract research organizations to an entity's centralized electronic laboratory notebook. The method may include collecting, by an entity computing device, over a network, data from one or more contract research organizations where the data is collected from local electronic notebooks corresponding to the contract research organizations. The one or more contract research organizations may include a single research entity having multiple research sites, or it may include multiple distinct research organizations. Each of the local electronic notebooks may have the same configuration as the centralized electronic-laboratory-notebook. The content of each of the local electronic notebooks may be limited to content specific to the respective contract research organization. The entity may include a corporate sponsor-company. The collection of data may be performed at the site of the contract research organization. The collection of data may be performed at an external server. The collection may be performed in a scheduled manner without any interaction by an end-user after the schedule is configured. The collection may be performed over a VPN connection. The collection may be performed over a SSL connection. The collection may be performed across a firewall.

In some implementations, the method may include automatically synchronizing, by the entity computing device, the data collected from the contract research organizations with data contained in the centralized electronic-laboratory-notebook. In some implementations, the data collected from the one or more contract research organizations by the entity computing-device may first be collected by a remote entity-server prior to the collection by the entity computing-device and prior to synchronization by the entity computing device with the centralized electronic laboratory notebook data.

In some implementations, the method may further include causing, by the entity computing device, a notification to be sent upon a successful update of the collection of the CRO data, a failed update, a modification of a scheduled job, or a creation of scheduled update.

In one aspect, the present disclosure describes a system including a processor and a memory, the memory storing instruction that, when executed by the processor, cause the processor to collect, by an entity computing device, over a network, data from one or more contract research organizations where the data is collected from local electronic-laboratory-notebooks corresponding to the contract research organizations. Each of the local electronic-laboratory-notebooks may have the same configuration as the centralized electronic-laboratory-notebook. The content of each of the local electronic-laboratory-notebooks may be limited to content specific to the respective contract research organization. The one or more contract research organizations may include a single research-entity having multiple research-sites, or it may include multiple distinct research-organizations. The entity may include a corporate sponsor-company. The collection of data may be performed at the site of the contract research organization. The collection of data may be performed at an external server. The collection may be performed in a scheduled manner without any interaction by an end-user after the schedule is configured. The collection may be performed over a VPN connection. The collection may be performed over a SSL connection. The collection may be performed across a firewall.

In some implementations, the instructions may further cause the processor to automatically synchronize, by the entity computing device, the data collected from the contract research organizations with data contained in the centralized electronic-laboratory-notebook. In some implementations, the data collected from the one or more contract research organizations by the entity computing device may first be collected by a remote entity-server prior to collection by the entity computing-device and prior to synchronization by the entity computing-device with the centralized electronic-laboratory-notebook data.

In one aspect, the present disclosure describes a non-transitory computer readable medium having instructions stored thereon, where the instructions, when executed by a processor, cause the processor to collect, by an entity computing device, over a network, data from one or more contract research organizations where the data is collected from local electronic-laboratory-notebooks corresponding to the contract research organizations. The one or more contract research organizations may include a single research entity having multiple research sites, or it may include multiple distinct research organizations. Each of the local electronic-laboratory-notebooks may have the same configuration as the centralized electronic-laboratory-notebook. The content of each of the local electronic-laboratory-notebooks may be limited to content specific to the respective contract research organization. The entity may include a corporate sponsor-company. The collection of data may be performed at the site of the contract research organization. The collection of data may be performed at an external server. The collection may be performed in a scheduled manner without any interaction by an end-user after the schedule is configured. The collection may be performed over a VPN connection. The collection may be performed over a SSL connection. The collection may be performed across a firewall.

In some implementations, the instructions may further cause the processor to automatically synchronize, by the entity computing device, the data collected from the contract research organizations with data contained in the centralized electronic laboratory notebook. In some implementations, the data collected from the one or more contract research organizations by the entity computing-device may first be collected by a remote entity-server prior to collection by the entity computing device and prior to synchronization by the entity computing-device with the centralized electronic-laboratory-notebook data.

In one aspect, the present disclosure describes a method of secure upload and management of data from one or more contract research organizations to an entity's centralized electronic-laboratory-notebook. The method may include scheduling, by an entity computing-device, a transfer of data collected from one or more contract research organization to an entity's centralized electronic-laboratory-notebook where the data is collected from local electronic-laboratory-notebooks corresponding to the contract research organizations. Each of the local electronic-laboratory-notebooks may have the same configuration as the centralized electronic-laboratory-notebook. The data of each of the local electronic-laboratory-notebooks may be limited to content specific to the respective contract research organization.

In some implementations, the scheduling may include an exporting action of the data. The scheduling may include an importing action the data. The scheduling may include a deleting action the data. The scheduling may be configured over a Web interface. The scheduling may further include identifying a type of data set for the transfer.

In some implementations, the method may include automatically deleting from the local electronic-laboratory-notebooks, by the entity computing device, the data collected from the contract research organizations after the scheduled transfer.

In one aspect, the present disclosure describes a system including a processor and a memory, the memory storing instruction that, when executed by the processor, cause the processor to schedule, by an entity computing device, a transfer of data collected from one or more contract research organizations to an entity's centralized electronic-laboratory-notebook where the data is collected from local electronic-laboratory-notebooks corresponding to the contract research organizations. The one or more contract research organizations may include a single research entity having multiple research sites, or it may include multiple distinct research organizations. Each of the local electronic-laboratory-notebooks may have the same configuration as the centralized electronic-laboratory-notebook. The data of each of the local electronic-laboratory-notebooks may be limited to content specific to the respective contract research organization.

In some implementations, the scheduling may include an exporting action of the data. The scheduling may include an importing action the data. The scheduling may include a deleting action the data. The scheduling may be configured over a Web interface. The scheduling may further include identifying a type of data set for the transfer.

In some implementations, the instructions may further cause the processor to automatically delete from the local electronic-laboratory-notebooks, by the entity computing device, the data collected from the contract research organizations after the scheduled transfer.

In one aspect, the present disclosure describes a non-transitory computer readable medium having instructions stored thereon, where the instructions, when executed by a processor, cause the processor to schedule, by an entity computing device, a transfer of data collected from one or more contract research organizations to an entity's centralized electronic-laboratory-notebook where the data is collected from local electronic-laboratory-notebooks corresponding to the contract research organizations. Each of the local electronic-laboratory-notebooks may have the same configuration as the centralized electronic-laboratory-notebook. The data of each of the local electronic-laboratory-notebooks may be limited to content specific to the respective contract research organization.

In some implementations, the scheduling may include an exporting action of the data. The scheduling may include an importing action the data. The scheduling may include a deleting action the data. The scheduling may be configured over a Web interface. The scheduling may further include identifying a type of data set for the transfer.

In some implementations, the instructions may further cause the processor to automatically delete from the local electronic-laboratory-notebooks, by the entity computing device, the data collected from the contract research organizations after the scheduled transfer.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 5A is an example graphical user interface of the E-Notebook data loader for scheduling a job in accordance with an embodiment of the invention.

FIGS. 5B and 5C are example graphical user interfaces of the E-Notebook data loader for modifying an existing job in accordance with an embodiment of the invention.

Figure 1:
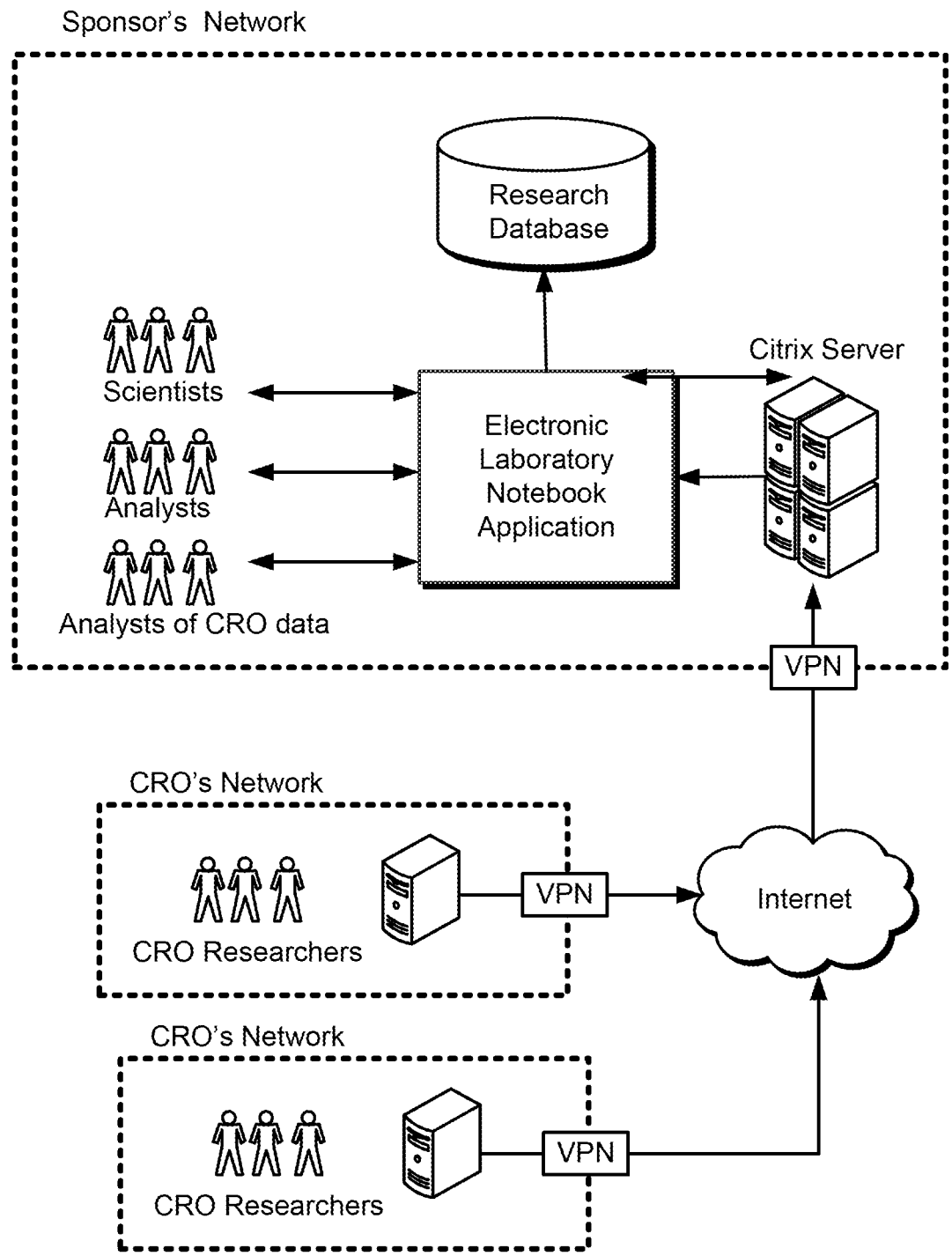
FIG. 1 is a prior art system for managing data between a contract-research-organization data and a sponsor company's electronic laboratory notebook ("E-Notebook").

The features and advantages of the present disclosure will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

Figure 2:
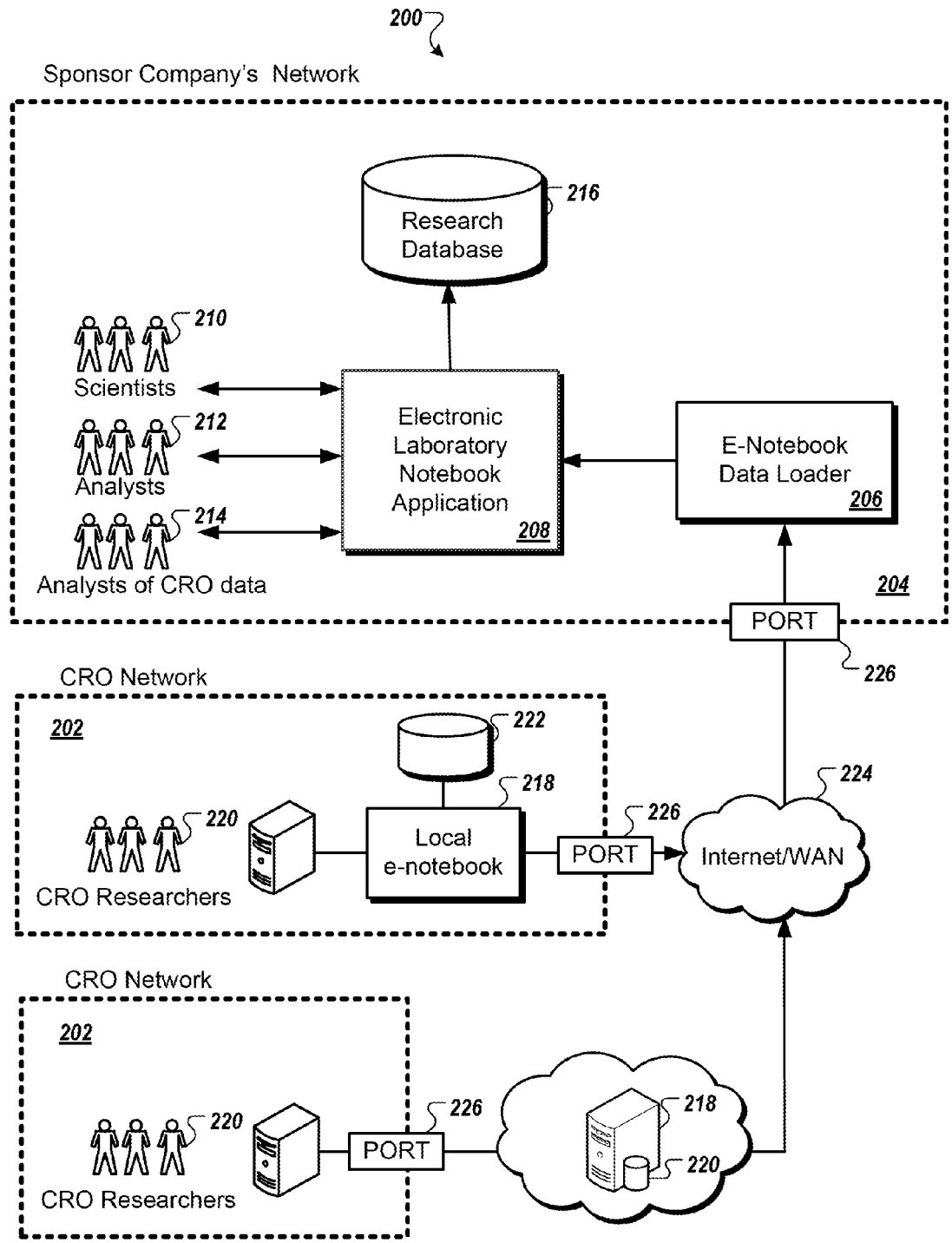
FIG. 2 is an example system for managing data exchanges between a contract research organization and a sponsor company's E-Notebook in accordance with an embodiment of the invention.

FIG. 2 is an example system 200 for managing data exchanges between a contract research organization (CRO) 202 and a sponsor company's electronic laboratory notebook ("E-Notebook") 204 in accordance with an embodiment of the invention.

In some implementations, the system 200 includes an electronic-laboratory-notebook data-loader 206 (also referred to as an "E-Notebook data loader 206") to interface with an electronic laboratory notebook 208 ("sponsor company E-notebook 208") located at the sponsor company 204. The sponsor company E-notebook 208 allows scientists 210, analysts 212, and analysts of CRO data 214 to access a research database 216 that stores the sponsor-company data and the CRO data. Alternatively, the sponsor central E-Notebook 208 may be hosted at a remote location and serviced by a third party vendor.

The E-notebook data loader 206 interfaces with a local electronic-laboratory-notebook 218 (also referred to as the "local E-Notebook 218") located preferably at a given CRO 202. The local E-Notebook is 218 allows scientists 220 located at the CRO 202 to record research data relating to the CRO's research services. The research data may be related to, for example, but not limited to, biopharmaceutical development, biologic assay development, commercialization, pre-clinical research, clinical research, clinical trials management, and pharma-covigilance, among other like research activity. In some implementations, the local E-Notebook 218 may be hosted at a remote location of the CRO 202. In some implementations, the local E-Notebook 218 may be hosted at the sponsor company 204 though separated from the sponsor company E-Notebook 208.

In some implementations, the communication exchange between the CRO 202 and the sponsor company E-notebook 208 occurs across a network infrastructure 224. This network infrastructure 224 may include the Internet, a Wide-area network, and/or a third-party network. Network security equipment 226 may secure the CRO 202 and the sponsor company E-notebook 208 within the network infrastructure. The network security equipment 226 that may run, for example, a firewall, a Network Address Translation (NAT) protocol, and/or other network security monitoring systems.

In some implementations, the local E-Notebook 218 interfaces with a local database 222 located preferably at the CRO 202. In some implementations, the local database 222 may be located at a remote location of the CRO 202. In some implementations, the local database 222 may be of the same type and configuration and the research database 216. Alternatively, the local database 222 may employ a different storage scheme that the local E-notebook 218 or the E-notebook data loader 206 may format to conform to that of the sponsor company E-notebook 208.

The E-notebook data loader 206 may perform scheduled (i.e., automatic) upload the CRO data into the sponsor company E-notebook 208 at predefined intervals. The predefined intervals may be hourly, daily, weekly, monthly quarterly or other defined periods of time. Once a record has been uploaded (such as by export or import mechanisms), the E-Notebook data loader 206 may perform scheduled (i.e., automatic) synchronization of the CRO data to upload updates to the CRO data to the sponsor company E-notebook 208 at predefined intervals. Moreover, subsequent to an upload or a synchronization action, the E-Notebook data loader 206 may automatically delete the CRO data from the local E-Notebook 218.

In certain embodiments, the E-Notebook data loader 206 supports "on-demand" uploading, particularly for more frequent upload CRO data, as well as non-scheduled CRO collections. The "on-demand" upload may be initiated by administrators or scientists at the CRO 202 or at the sponsor company 204.

In some implementations, the E-Notebook data loader 206 may support synchronization of "signed-and-closed" CRO collections with the main corporate E-Notebook. "Signed-and-closed" refers to a complete research project that has been approved by the CRO scientist to transfer to the sponsor company.

The CRO data may be uploaded to the sponsor company E-notebook 208 in a secure manner, such as via VPN or SSL. Various encryption and data security methods may be employed.

To promote privacy and IP protection, the E-Notebook data loader 206 allows the administrator of the sponsor company 204 to block the CRO scientists 220 from access of the sponsor company E-notebook 208 and the research database 216.

To promote efficient research operation at the CRO 202, the local E-Notebook 218 allows the CRO scientists 220 to record their research as the research is on-going. The research record may be subsequently uploaded or synchronized without impact to the sponsor company E-notebook 208.

In some implementations, the E-Notebook data loader 206 may include a configuration panel to schedule uploading and synchronization jobs. The configuration panel may be controlled by an administrator of the sponsor company to schedule the data exchange of the CRO data during runtime. The administrator may configure, via the configuration panel, the E-notebook data loader 206 by providing routing and login information of the sponsor company E-notebook 208 and the CRO local E-Notebook 218. Such configuration information may include, for example, IP address and login information, and the like.

The configuration panel may be used to associate a CRO researcher to a given set of research record. To this end, records of various research projects may be easily identified. The association moreover reduces the risk of a given research project being incorrectly analyzed by a given analyst or analysis system.

In some implementations, the E-Notebook data loader 206 may transmits alert and notification. The alert or notification is preferably generated as a status report that provides a status of a data upload or synchronization or delete action. The report is transmitted preferably as an email notification.

To avoid validation and testing, in some implementations, the E-Notebook data loader 206 may be configured to operate independently of the sponsor company E-notebook 208. The E-Notebook data loader 206 may utilize native exporting and importing functions of the sponsor company E-notebook 208 to upload or synchronize the CRO data. For example, the E-Notebook data loader 206 may use the native application programming interface (API) of the E-Notebook. An export job of the E-notebook data loader 206 may employ, for example, an export function for "signed-and-closed" collections. The import job may employ import functions for "new" items in the E-Notebook database or collections that may be "merged" into the E-Notebook database. The E-Notebook data loader 206 may, for example, insert a CRO collection as a new collection to the research database 216. The E-Notebook data loader 206 may support "push" or "pull" data with the sponsor company E-notebook 208. In some implementations, a "push" function may be implemented as an import function by the sponsor company E-notebook 208. In some implementations, a "poll" function may be implemented as an export function at the local E-Notebook 218.

In some implementations, the E-Notebook data loader 206 allows the data synchronization to occur in a single direction from the CRO 202 to the sponsor company E-notebook 208. To this end, imported collections of the research record may be designated as "read-only" to avoid version control during synchronization. In some implementations, to simplify the implementation, the local E-Notebook 218 may interface to a local database 222 or semantic database model (SDM).

In some implementations, the hardware requirements for the E-Notebook Data Loader 206 is preferably the same as the local E-Notebook 218. To this end, the E-Notebook data loader 206 may be installed on the same system as the sponsor company E-notebook 208. Alternatively, the E-Notebook data loader 206 may be installed on a separate hardware to avoid validation concerns.

In some implementations, the local E-Notebook 218 may be installed on an all-in-one workstation or a traditional "three-tier" workstation. The "three-tier" workstation may be utilized to minimize the number of user licenses.

Figure 3:
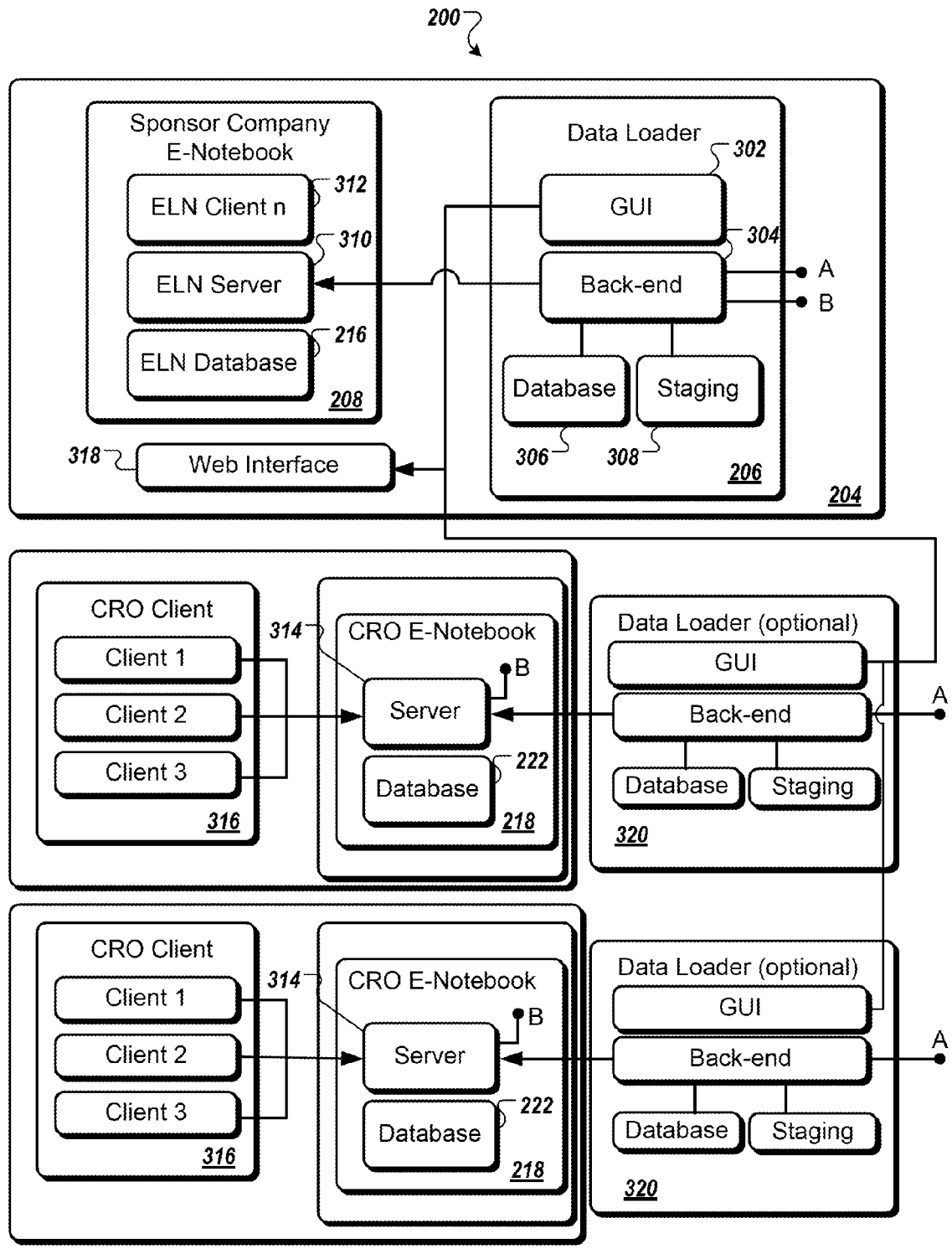
FIG. 3 is a diagram of an example system for managing data exchanges between a contract research organization and a sponsor company's E-Notebook in accordance with an embodiment of the invention.

FIG. 3 is a diagram of the example system 200 for managing data exchanges between a contract research organization 202 and a sponsor company's electronic laboratory notebook 204 in accordance with an embodiment of the invention.

In some implementations, the system 200 includes the E-Notebook data loader 206, the sponsor company E-notebook 208, and the local E-Notebook 218, as described in relation to FIG. 2.

In some implementations, the E-Notebook data loader 206 includes a graphical user interface 302, a back-end service 304, a download database 306, and a Data Loader Staging component 308.

The graphical user interface 302 allows an end-user to interface to the back-end services 304, which includes the control functions to export, import, delete, and synchronize the CRO data from the CRO 202 with the sponsor company E-notebook 208. The graphical user interface 302 may include a command-line function that allows commands to be inputted by text commands. The Data Loader Staging component 308 may be a temporary buffer to receive the CRO data from a given CRO 202. For example, the Data Loader Staging component 308 may store extracted XML files utilized during a transfer. The back-end services 304 may organize the data in the Data Loader Staging 308 into a pre-defined format corresponding to the research database 216 or the sponsor company E-notebook 208. The formatted data record may be stored in the database 306 of the E-Notebook data loader 206.

In some implementations, the back-end services 304 transmit (such as by push or pull mechanisms) the server component 310 of the sponsor company E-notebook 208. A given sponsor company E-notebook 208 may include the server component 310, the research database 216 and/or the client component 312. In some implementations, the server component 310 manages the data records from the client component 312 of the sponsor company E-notebook 208 and from the E-Notebook data loader 206. The client component 312 may be the front-end application to which researchers and scientists 210 and analysts 212 of the sponsor company 204 may record experimental data and analysis.

In some implementations, a given local E-Notebook 218 may include a server component 314, the local database 222 and the client component 316.

The server component 314 may manage data records from the client component 312 of the contract research organization 202. The server component 314 of the local E-Notebook 218 may interface with the back-end component 304 of the E-Notebook data loader 206. In some implementations, the server component 314 of the local E-Notebook 218 is the same as the server component 310 of the sponsor company E-notebook 208.

The client component 316 may be the front-end application to which researchers and scientists 220 may record experimental data and analysis at the CRO 202. In some implementations, the client component 316 of the local E-Notebook 218 is the same as the client component 312 of the sponsor company E-notebook 208.

In some implementations, the system 200 may include a Web interface 318 for interfacing to the graphical user interface 302 of the E-Notebook data loader 206 as well as the interface of the local E-Notebook 218. The interface of the local E-notebook 218 may be at the server component 314 or an optional data loader 320. The optional data loader 320 may coordinate the interface between the local E-Notebook 218 and the E-Notebook data loader 206. In some implementations, the optional data loader 320 may be the same as the E-Notebook data loader 206. In some implementations, the back-end components of the optional data loader 320 may connect (see "line A") and synchronize with the back-end component of the E-Notebook data loader 206.

Figure 4:
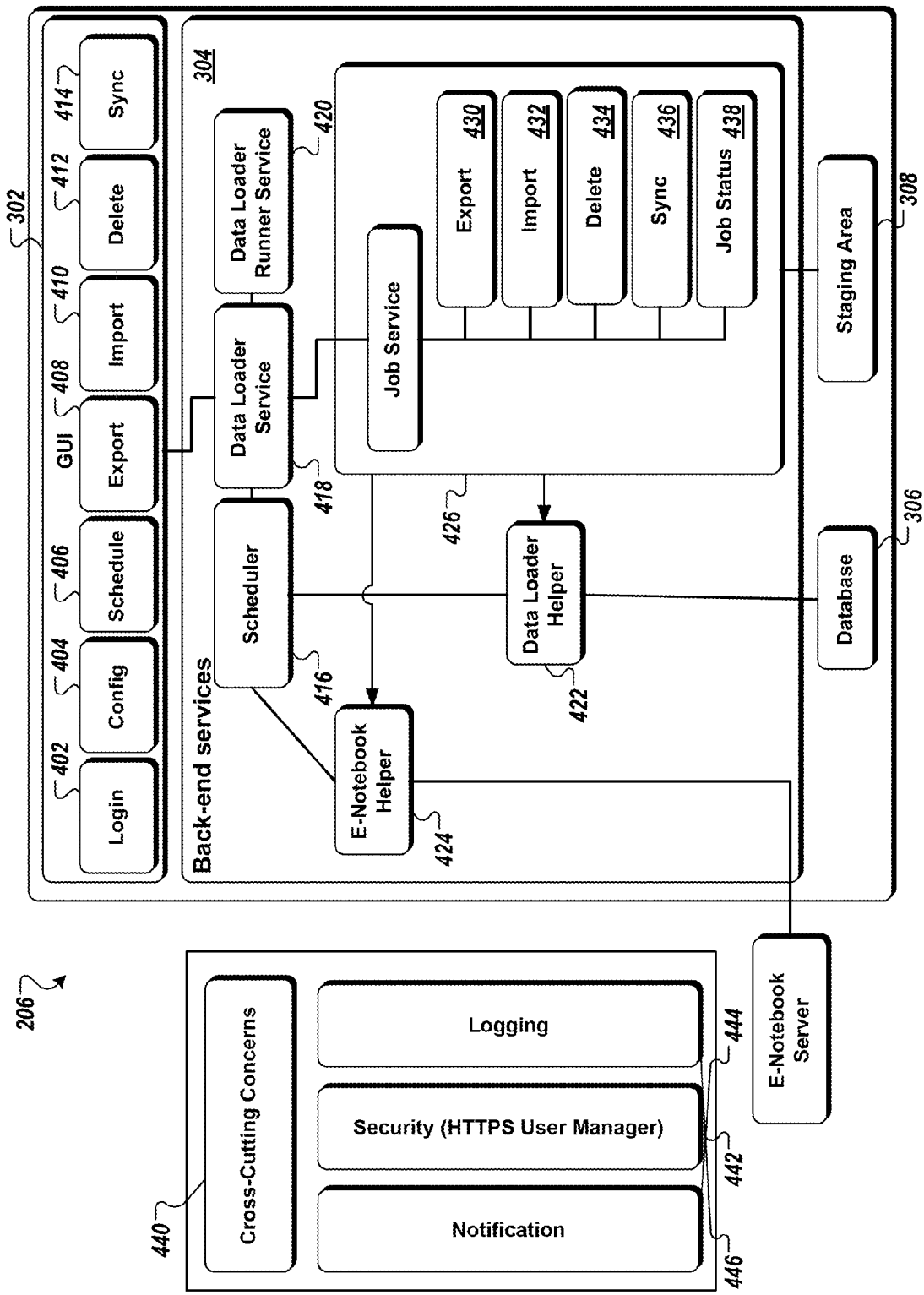
FIG. 4 is a diagram of an example E-Notebook data loader in accordance with an embodiment of the invention.

FIG. 4 is a diagram of an example electronic laboratory notebook ("E-Notebook") data loader 206 in accordance with an embodiment of the invention.

In some implementations, the E-Notebook data loader 206 includes the graphical user interface 302, the back-end services 304, the database 306, and the Data Loader Staging component 308, as described in relation to FIG. 3.

The graphical user interface 302 may include a login component 402 for an end-user or an administrator to access the E-Notebook data loader 206. The login component 402 may be a Web service that allows access, in some implementations, via any Web browser.

The graphical user interface 302 may include a configuration component 404 for adding, modifying, and deleting the server information associated with the sponsor company E-notebook 208 and the local E-Notebook 218. The configuration component 404 allows the E-Notebook data loader 206 to add both remote servers and local servers. An administrator may configure, at the configuration component 404, both the remote server and the local server to configure the various jobs of the E-Notebook data loader 206. In relation to the E-notebook data loader 206, a remote E-Notebook server may be the local E-Notebook 218 whereas a local E-Notebook server may be the sponsor company E-notebook 208. The configuration panel may display the server name, the server type, and a user name associated with the server.

The graphical user interface 302 may include a scheduler component 406 for creating and modifying the schedule of the E-Notebook data loader 206 to perform a job. A job may include exporting, importing, deleting, syncing, and/or reporting action.

FIG. 5A is an example graphical user interface 502 of the E-Notebook data loader for scheduling a job in accordance with an embodiment of the invention. As shown, the graphical user interface 502 includes inputs for a job-information and the CRO data information. The job information may include a job name 504, a job type 506, a state identifier 510, and the action time 512. For scheduled action, the panel 502 may include a start time 514 and a recurring-information 516. A given job may also be designated as active or inactive. To this end, an administrator may temporarily stop a given job and reinitiate it at a subsequent time. The CRO data information may include an identifier 518 of the local E-Notebook 218, a research-owner identifier 508, and a collection type 520. The job types 506 may allow for export, delete, import, and sync. The graphical user interface 502 may include an input 517 to initiate a schedule action.

Figure 6:
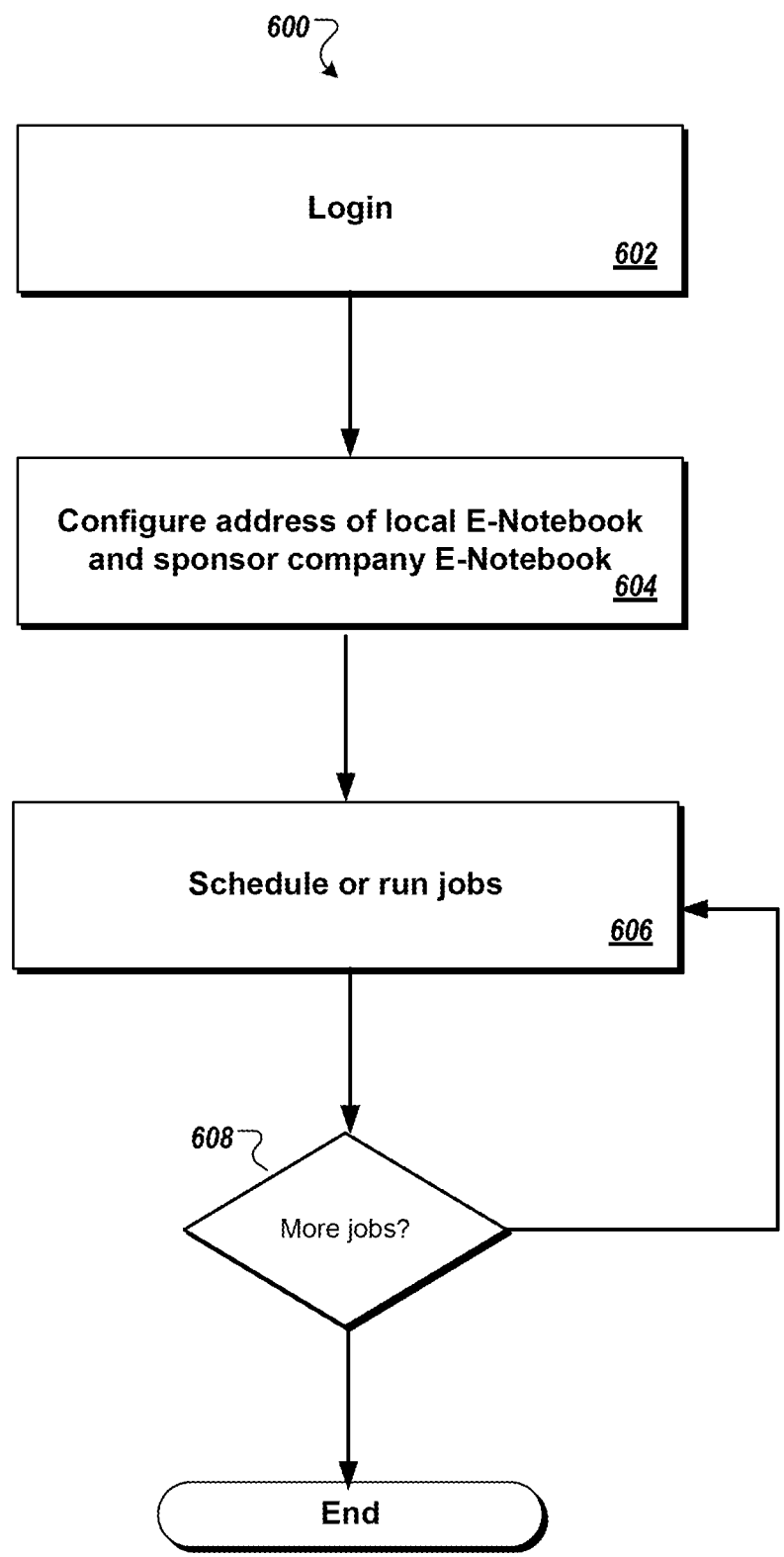
FIG. 6 is a flowchart diagram showing an example method of scheduling a job using the E-Notebook data loader in accordance with an embodiment of the invention.

FIG. 6 is a flowchart diagram showing an example method 600 of scheduling a job in using the E-Notebook data loader in accordance with an embodiment of the invention.

The method 600 typically begins with an administrator at a sponsor company logging into the graphical user interface 302 of the E-Notebook data loader 206 (step 602). In some implementations, the graphical user interface 302 may be access via the Web interface 318. The administrator may then configure the address information for the local E-Notebook 218 associated to given CRO servers (step 604). In some implementations, the administrator merely inputs the address information for the local E-Notebook 218, the server type, record description, and a username and password to access the local E-Notebook 218. The address information may include a Web Service path to the local E-Notebook 218 service or a name of a server hosting the service, as well as a database configuration file. In some embodiments, the database configuration file is a database definition file, such as an Oracle XML configuration file, that is used to parse the record. The record description may include a name for the collection and an identifier of collection per container. The graphical user interface 302 may include an input to permanently delete a record from the local E-Notebook 218 after a delete action, which may be executed after an upload or update of the CRO data. The server type may be designated as "remote" as the local E-Notebook 218 is remotely installed to the E-Notebook data loader 206.

Similarly, the administrator may then configure the address information for the sponsor company's E-Notebook 208 (step 604). In some implementations, the administrator merely inputs the address information for the local E-Notebook 208, the server type, record description, and a username and password to access the sponsor company's E-Notebook 208. The address information may include a Web Service path to the sponsor company's E-Notebook 208 service or a name of a server hosting the service, as well as a database configuration file. In some embodiments, the database configuration file is a database definition file, such as an Oracle XML configuration file, to parse the record. The record description may include a name for the collection once imported and an identifier of how the collection is organized. The graphical user interface 302 may include a command to delete any temporary data set employed during the record transfer after a record is successfully imported. The server type may be designated as "local" as the sponsor company's E-Notebook 218 is locally installed in relation to the E-Notebook data loader 206.

Subsequent to configuring the local E-Notebook 218, the administrator can add a job action, such as an export or import action (step 606). The export action may be directed to the local E-Notebook 218 to push the CRO data to the sponsor company E-notebook 208. The import action may be directed to the sponsor company E-notebook 208 to pull the CRO data from the local E-Notebook 218. The administrator can specify whether to run the job now, to schedule it for later, or to schedule the job now and also run it now. The administrator can specify whether the administrator wish to receive a notification of the action being completed or failed. The administrator can also specify whether to delete the CRO data or any temporary files at the research database 216 once the import or export action is complete. After an action is added, the action is displayed in a list of actions that the administrator can modify or delete. The administrator may also designate a job as active or inactive. To this end, the administrator may temporary stop certain jobs and reactivate them later.

The administrator may add a synchronization action for an existing record set. The sync may append or merge updated CRO data to the sponsor company E-notebook 208. In some implementations, the update bypasses the sponsor company E-notebook 208 and is directly merged to the research database 216. Similarly, the administrator may specify that the E-Notebook data loader 206 deletes the synchronized CRO data once the action is complete.

The administrator can add additional jobs to run now or schedule them for later as desired (step 608).

To improve the navigability of the graphical user interface 302, the interface may be configured to display only actions that are available to a given end-user based on the selection the end-user has already made.

Figure 7:
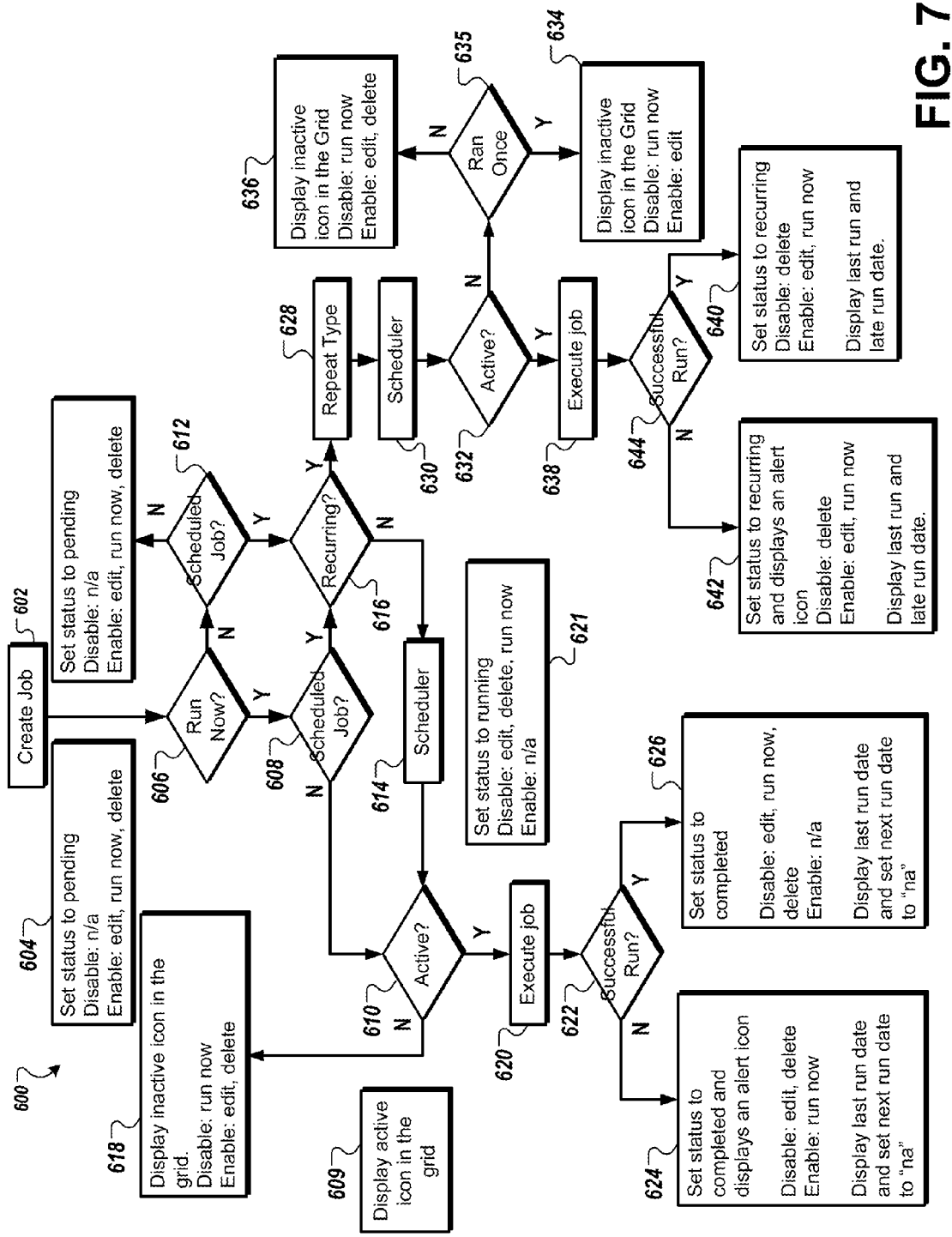
FIG. 7 is a flowchart diagram showing an example method of scheduling a job using the E-Notebook data loader in accordance with an embodiment of the invention.

FIG. 7 is a flowchart diagram showing an example method 700 of scheduling a job using the E-Notebook data loader in accordance with an embodiment of the invention.

In some implementations, the graphical user interface 302 includes several types of inputs, including schedule job, run now, notify me, recurring, and active. The graphical user interface 302 may display various inputs or remove inputs from display based on the end-user input selections while the end-user is configuring a job.

The method 700 may be initiated 602 by a "create job" input 517 being received at the E-Notebook data loader 206, as described in relation to FIG. 5A. In some implementations, the method 700 initiates and sets 604 the job status to "pending." The graphical user interface 302 may accept an edit, run now, and/or delete action to be selected by the end-user.

The method 700 may then determine (606 and 608, respectively), whether the action 512 associated with the "run now" 512*a* and the "scheduled job" 512*b* have been selected. If "run now" 512*a* has been selected (606) and "scheduled job" 512*b* was not selected (608), the method 700 may display 609 the active input 512*c*. If the job is not active (610), the method 700 may terminate the workflow by displaying 618 that the job is inactive while also disabling the "run now" command and enabling the "edit" and "delete" command. If the method 700 determined 610 that the job is active 512*c*, the method 700 may execute 620 the job by calling on the appropriate job runner module 426. In some implementations, the job runner modules may include an Export Job Runner, an Import Job Runner, or a Delete Job Runner. During execution, the graphical user interface 302 may display 621 the job status as "running" and disable the invoking of the edit, delete, and run now commands at the graphical user interface 302.

Subsequent to a job execution, the method 700 may determine 622 if the run was successful. If not successful, the method 700 may set 624 the job status as "completed" and displays an alert icon. The method may also disable the "edit" and "delete" command from the graphical user interface 302 and enable the "run now" command. If successful, the method 700 may set 626 the job status as "completed." The method may also disable the "edit", "run now", and "delete command" at the graphical user interface 302.

Referring back to the "run now" determination 606, if "scheduled job" 512*b* has been selected (see 608 and 612) and "recurring" 516 was not selected 616, the method 700 may add 614 the job to the scheduler 416 before determining 610 if the job is active.

If a job is designated 616 as "recurring," the method 700 may include using 628 the "repeat type" selected at the graphical user interface 302 and then add 630 the job action to the scheduler 416. The "repeat type" 612 may include hourly, daily, weekly, monthly, and others. The method 700 may then determine 632 if the job is active 512*c*.

If the method 700 determines 632 that the job is not active 512*c*, the method 700 ends the work-flow by displaying that the job is inactive. If the job had ran once 635, the method 700 may display 634 that the job can be edited. If the job had not run once 635, the method 700 displays 636 that the job can be edited or deleted.

Returning to the recurring determination 616, if the method 700 determines 632 that the job is active 512*c*, the method 700 executes 638 the job by calling on the appropriate job runner module 426. The method 700 displays 640, 642 the job as recurring along with the last-run- and run-date. If the method 700 determines 644 that the job was unsuccessful, the method 700 displays 642 an alert. The above example serves merely as an illustration. Of course, rules, sequential logic, and other controls means may be employed to configure the export workflow and graphical user interface 302.

Referring back to FIG. 4, in some implementations, the graphical user interface 302 may include an export component 408, an import component 410, a delete component 412, and a sync component 414. These components 408, 410, 412, and 414 may provide a list of the on-going jobs for a given action type. Each of these components also allows a given type of job to be run now.

The back-end services 304 includes the control functions to export, import, delete, and synchronize the CRO data from the CRO 202 with the sponsor company E-notebook 208. In some implementations, the back-end services 304 may include a Data Loader Job Scheduler 416 (referred to as "Scheduler 416"), a Data Loader Service 418, a Data Loader Runner Service 420, a Data Loader Helper 422, an E-notebook Helper 424, and the job runner modules 426.

In some implementations, the Data Loader Service 418 may be a Web Service that centralizes the management of the user interfaces and network connections among the Data Loader servers, Web browser, and E-Notebook systems. The Data Loader Service 418 may provide an API for syncing between the Data Loader services, for example, where the optional Data Loader 320 is employed. The Data Loader Service 418 may manage the jobs and the server configurations associated with the E-Notebook data loader 206. The Data Loader service 418 may operate in conjunction with the Data Loader Runner Service 420, which executes the different synchronization and export jobs. The Data Loader Service 418 may include functions to add jobs, to update jobs, to delete jobs, to get jobs, to update job active status, to run scheduled jobs, to run now, and to get sync data.

In some implementations, the Data Loader Job Scheduler 416 may allow one or more users to schedule and manage different synchronization jobs.

To execute a job, the Data Loader Runner Service 420 may dispatch a pipeline operation to a given job action via the operating system's service calls. The Data Loader Runner Service 420 that can initiate jobs based on scheduled activities provided by the Data Loader Job Scheduler 416.

In some implementations, the Data Loader Helper 422 and the E-notebook helper 424 may provide an interface to the research database 216 and the local E-Notebook 218, respectively. The Data Loader Helper 422 and the E-notebook helper 424 may be initiated from the schedule 416, which receives the appropriate CRO data from the various action modules.

In some implementations, the job runner modules 426 may include an Export Job Runner 430, an Import Job Runner 432, a Delete Job Runner 434, a Sync Job Runner 436, and a Job Status Job Runner 438. The job service module 428 may call the modules 432, 434, 436, and 438 based on the inputs 406, 408, 410, 412, and 414 selected at the graphical user interface 302.

The E-notebook data loader 206 may include a Data Loader Cross-Cutting Concern Manager 440 that can handle different cross-cutting concerns, such as security component 442, notifications and alerts component 444, login component 446, and the like. The login component 446 allows an administrator to provide information to access the E-Notebook data loader 206 as well as for the E-Notebook data loader 206 to access the local E-Notebook 218 and the sponsor company E-Notebook 208. The login component 446 may operate in conjunction with the security component 442. In some implementations, the security component provides an interface to operate with a third-party public-key cryptosystem. An example of such a system includes that provided by RSA Security LLC.

The notifications and alerts component 444 allows the E-Notebook data loader 206 to send notification of action status as well as alerts of action errors. A notification may be generated as an electronic mail (e-mail) in which the administrator can designate an address. The E-Notebook data loader 206 may generate notification for (i) when a specific job succeeds for (ii) when a specific job fails; (iii) when a specific job detail is modified; and (iv) when a new job is created by a specific user.

FIGS. 5B and 5C are example graphical user interfaces 525 for modifying an existing job in accordance with an embodiment of the invention. Each of the graphical user interfaces 525 may include a list 526 of jobs. The list 526 may include an input 528 to modify the action, for example, to delete or to schedule an action. The graphical user interface 525 may include an identifier 530 of the local E-Notebook 218 associated with action and the owner 532 of the action. The owner may be an identifier (such a username) of the CRO researcher 220 to which the record is associated.

The functions of the job runner modules 426 are now discussed.

Figure 8:
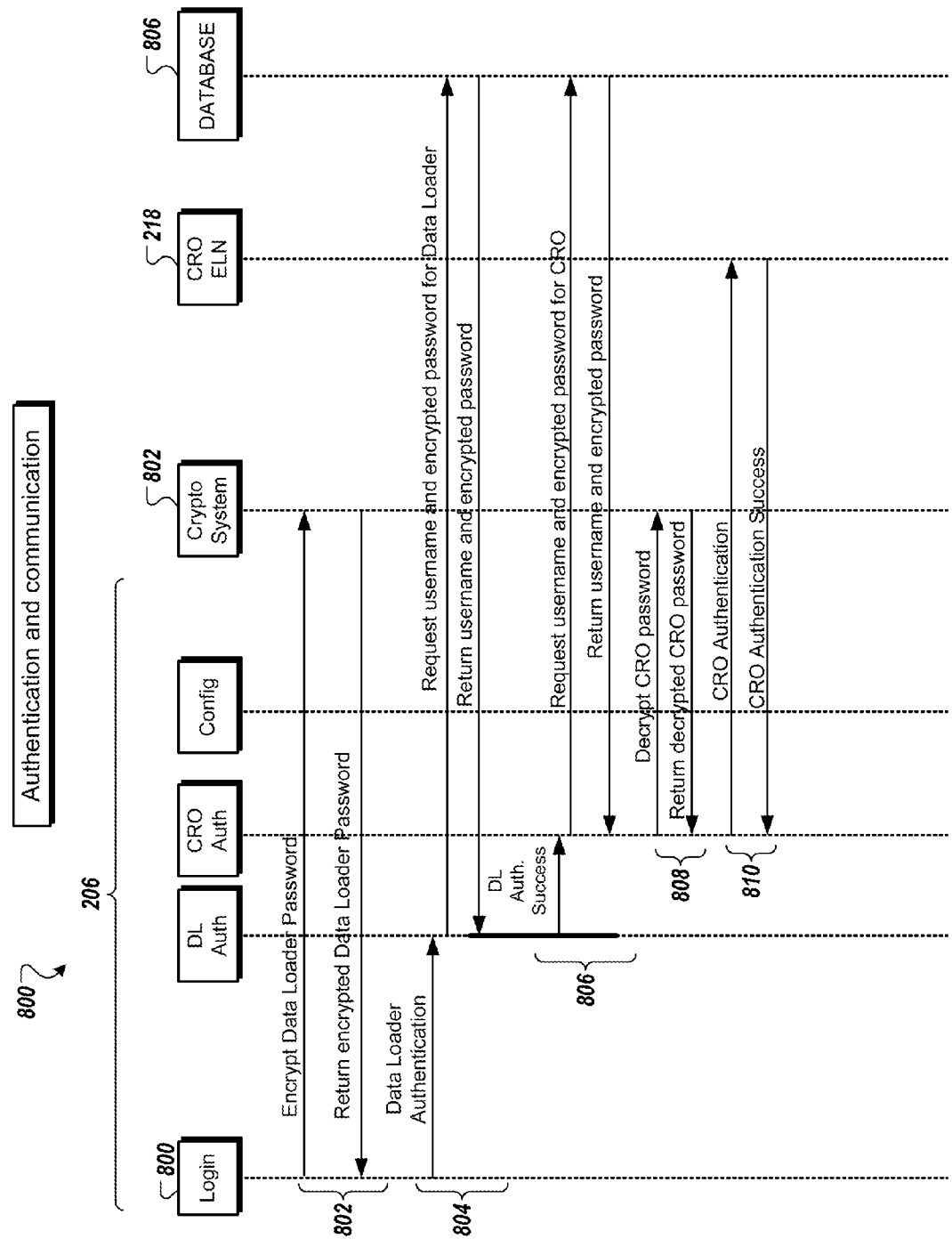
FIG. 8 is a swim-lane diagram of an example method of authenticating a data exchange session between a contract research organization and a sponsor company's E-Notebook in accordance with an embodiment of the invention.

FIG. 8 is a swim-lane diagram of an example method 800 of authenticating a data exchange session between a contract research organization 202 and a sponsor company's electronic laboratory notebook 208 in accordance with an embodiment of the invention. The method 800 allows for a secure session to be established among the E-notebook data loader 206 and the local E-notebook 218 to access the CRO data of the local E-Notebook 218.

In some implementations, when an administrator is adding a local E-notebook 218 to the E-Notebook data loader 206, the method 800 includes the E-Notebook data loader 206 retrieving an encrypted public-key from a third-party cryptosystem 802 (step 802). An example of such third-party cryptosystem 802 includes the RSA cryptosystem. The encrypted public-key may be retrieved using a password or pin provided by the administrator at a login panel of the graphical user interface 302.

The administrator may use the retrieved encrypted public-key to authenticate his or her credentials to access the E-Notebook data loader 206 (step 804). The encrypted public-key may be transmitted to an authentication database 806 to request for a username and password for the E-Notebook data loader 206. In some implementations, the authentication database 806 is the research database 216 of the sponsor company. Alternatively, the authentication database 806 is a local database configured as part of the E-Notebook data loader 206 or a remote authentication server. The authentication database 806 returns the username and encrypted password. A failed authentication may return the administrator to the main login page. If the authentication is a default password, the E-Notebook data loader 206 may prompt the administrator for a new or updated password.

Once the administrator has successfully authenticated his or her credentials to access the E-Notebook data loader 206, the administrator may call for an authentication of a local E-Notebook 218 located at the CRO 202 (step 806). This second authentication allows the E-Notebook data loader 206 to securely manage multiple local E-Notebooks 218 as each of the local E-Notebooks 218 may be independently authenticated. This authentication may be stored for the E-Notebook data loader 206 to run subsequent scheduled jobs.

To authenticate each of the local E-Notebooks 218, the method 800 may include sending a request to the authentication database 806 from the E-Notebook data loader 206 to request for a username and encrypted password (step 808). Once the authentication database 806 returns the username and encrypted password, the E-Notebook data loader 206 may send the username and encrypted password to the cryptosystem 802 to retrieve a CRO password (step 806). The E-Notebook data loader 206 may then use the CRO password to authenticate the CRO with the local E-Notebook 218 (step 810). Once authenticated, the E-Notebook data loader 206 may save the connection to the application session. If the CRO password had failed to authenticate the local E-Notebook 218, the graphical user interface 302 may prompt the administrator to the configuration panel where the administrator can provide another authenticate credential to access the local E-Notebook 218.

Figure 9A:
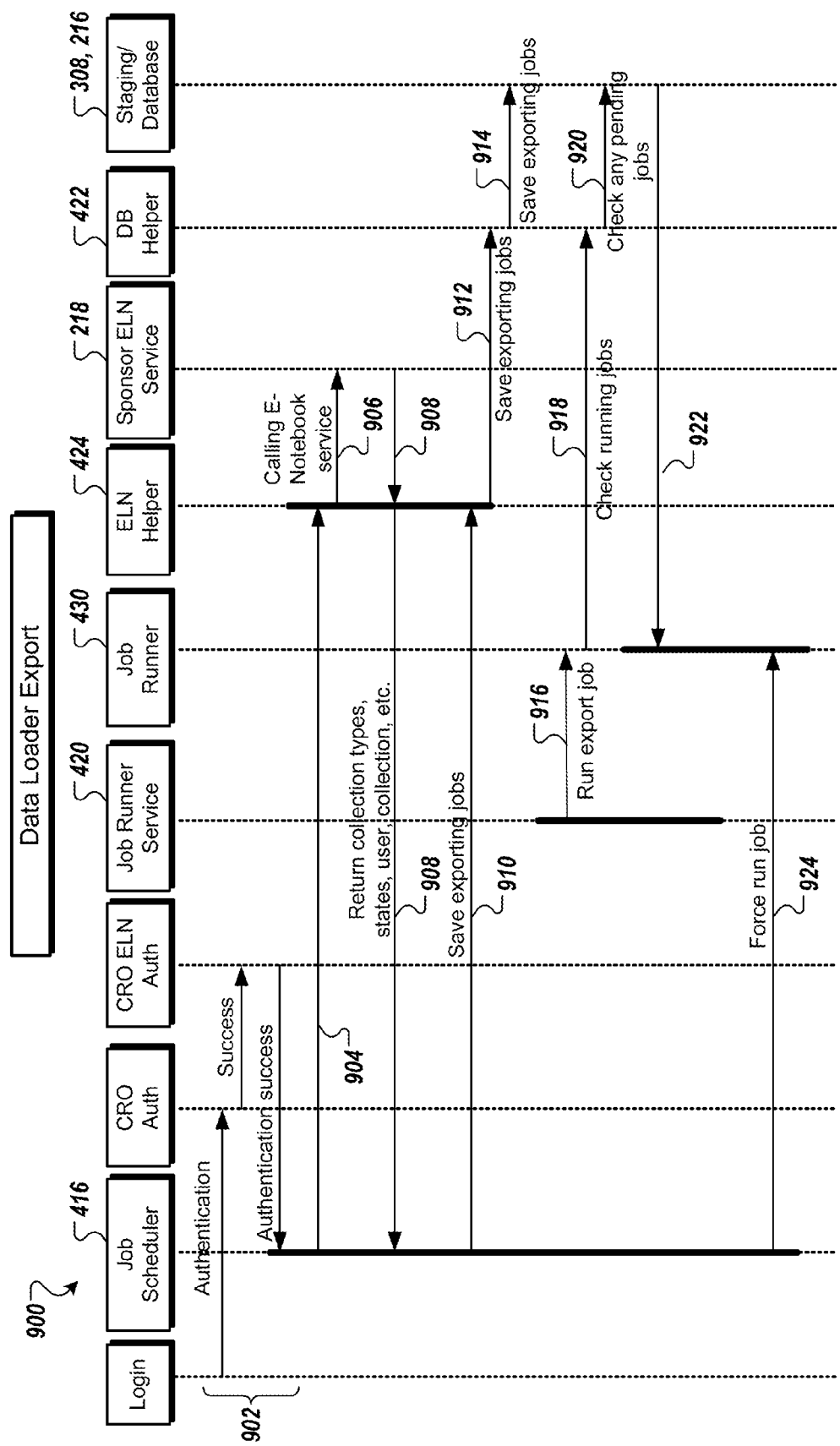
FIG. 9A is a swim-lane diagram of an example method of exporting data from a contract research organization to a sponsor company's E-Notebook in accordance with an embodiment of the invention.

FIG. 9A is a swim-lane diagram of an example method 900 of exporting data from a contract research organization 202 to a sponsor company's electronic laboratory notebook 208 in accordance with an embodiment of the invention. In some implementations, the E-Notebook data loader 206 may provide options to execute a job. These options may include running the job immediately, running at scheduled intervals, and running on demand.

In some implementations, the method 900 includes accessing the E-Notebook data loader 206 (step 902), as described in relation to FIG. 8. The method 900 may include adding or configuring an export action, as described in relation to FIGS. 4 and 5A. Once a scheduled export action has been created, updated, or made active, the Data Loader Job Scheduler 416 may initiate an export job once the schedule condition is met. In some implementations, the schedule condition may be based on time and date. In some implementations, the schedule condition may include server load condition at the sponsor company E-Notebook 208.

In some implementations, the E-Notebook data loader 206 may configure an export action by initiating a service call to the E-Notebook Helper 424 (step 904), which then transmit a service call to a given local E-Notebook 218 (step 906). The local E-Notebook 218 returns the request to the Data Loader Job Scheduler 416 through the E-Notebook Helper 424. The returned information may include a collection type description of a given research record, the record's state information, and the researcher's information associated with the record (step 908).

The administrator may save the export action as an export job, which is stored at the Data Loader Job Scheduler 416. The Data Loader Job Scheduler 416 may transmit the saved job to the E-notebook Helper 424 (step 910). The E-notebook Helper 424 may then transmit the saved job to the Data Loader Helper 422 (step 912) and to the Data Loader Staging component 308 and the research database 216 (step 914).

In some implementations, the Data Loader Runner Service 420 of the E-Notebook data loader 206 may initiate an export job using scheduled activities provided by the Data Loader Job Scheduler 416. When initiating a job, the Data Loader Runner Service 420 may call the Job Runner 430 to initiate an export action (step 916). The Job Runner 430 may check with the Data Loader Helper 422 to determine if there exist on-going jobs (step 918). The Data Loader Helper 422 may check the staging component 216 or the local Database 308 to determine if there exists other jobs in queue (step 920). If there are no pending jobs and no jobs pending, the Export Job Runner 430 is initiated (step 922).

If there is a job running, the Data Loader Runner Service 420 may initiate a service routine to recheck with the Data Loader Service 418 within a predefined time. In some implementations, the Data Loader Service 418 may add the check request from the Data Loader Runner Service 420 to its queue. Once the preceding actions are complete, the Data Loader Service 418 may send a trigger to the Data Loader Runner Service 420 to initiate its job.

In some implementations, Data Loader Job Scheduler 416 may force an export job to run immediately, for example, when the administrator selects a "run now" export action (step 924).

Figure 9B:
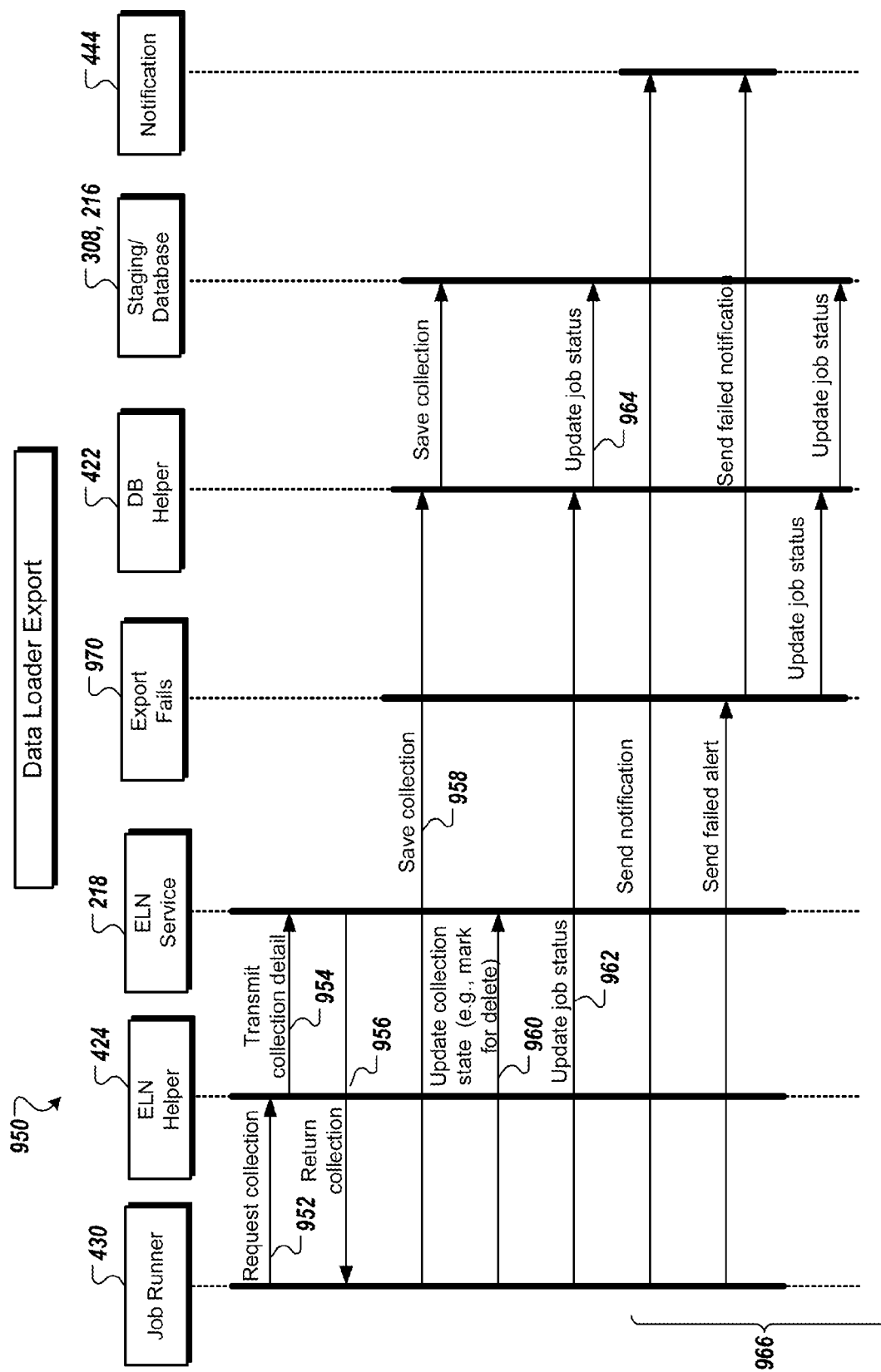
FIG. 9B is a swim-lane diagram of an example method of exporting data from a contract research organization to a sponsor company's E-Notebook in accordance with an embodiment of the invention.

FIG. 9B is a swim-lane diagram of an example method 950 of an export action to transfer data from a contract research organization 202 to a sponsor company's electronic laboratory notebook 208 in accordance with an embodiment of the invention. In some implementations, the method 950 may initiate with the Export Job Runner 430 sending an export action request to the E-Notebook Helper 424 (step 952). The E-Notebook Helper 424 then sends the export action request to a given local E-Notebook 218 (step 954). The local E-Notebook 218 returns a collection of requested records, including the CRO data, to the Export Job Runner 430 (step 956) as a reply to the export action request. The Export Job Runner 430 then sends the returned collection to the Data Loader Helper 422 (step 958), which then sends the collection to the Data Loader Staging component 308 and the research database 216.

In some implementations, the Export Job Runner 430 then sends an updated collection state to the local E-Notebook 218 (step 960). The collection state may include a "mark for delete" status. In some implementations, the Export Job Runner 430 then sends an updated job status to the Data Loader Helper 422 (step 962). The Data Loader Helper 422 then sends the status to the Data Loader Staging component 308 and research database 216 (step 964).

In some implementations, the Export Job Runner 430 sends an update to the notification and alert component 444 (step 966). The notification and alert component 444 may generate a notice (such as an email) of the status and send it to the designated notice party. In some implementations, the notice may be a short message service (SMS) or a log in a chat session.

If the export job was unsuccessful, the Export Job Runner 430 may send the failed status to an "export fail" state 970 (running within the E-Notebook data loader 206). The "export fail" state 970 may then send the failed status to the notification component 444 (step 972), to the Data Loader Helper 422 (step 974), and to the Data Loader Staging component 308 and research database 216 (step 976).

Figure 10:
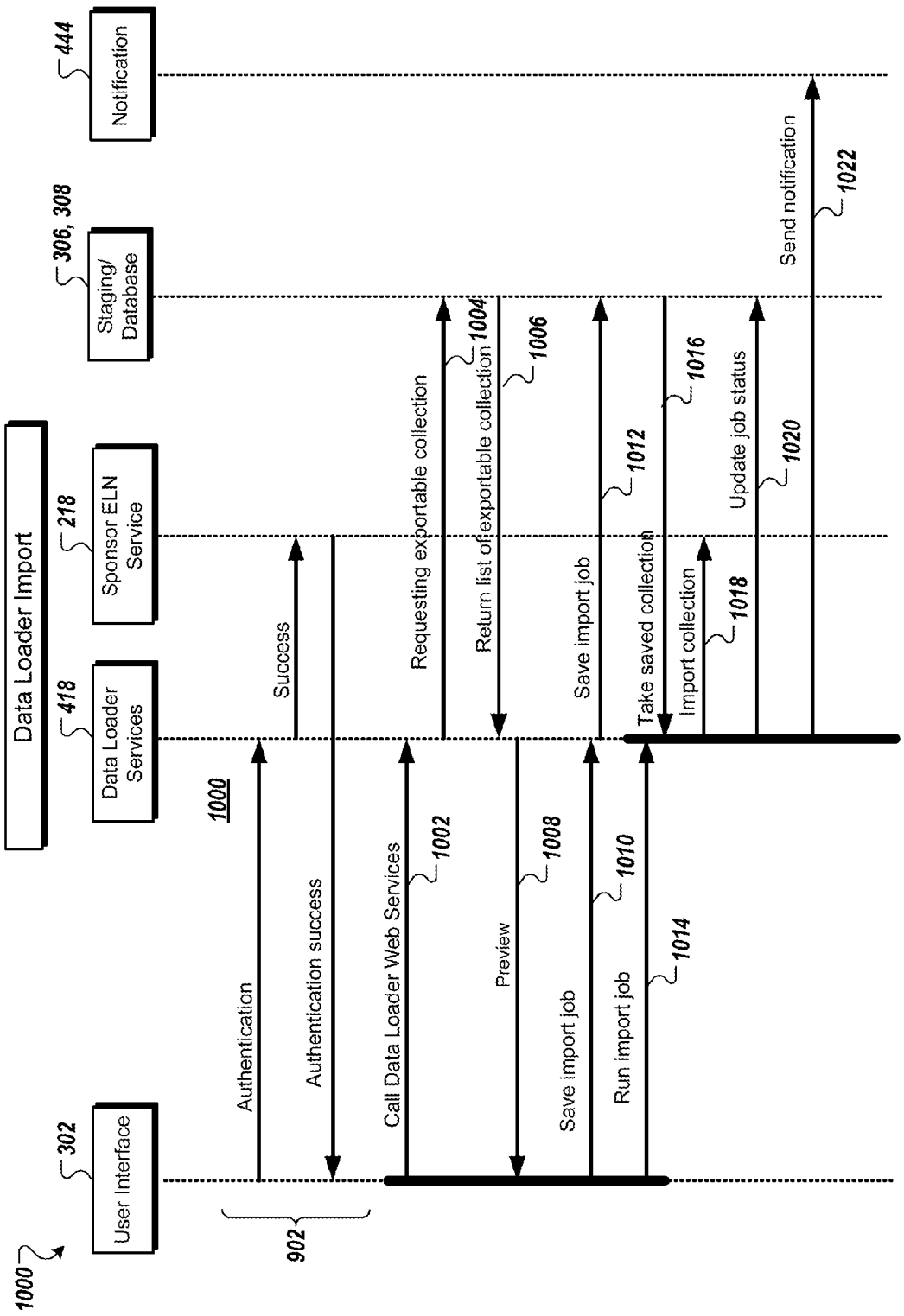
FIG. 10 is a swim-lane diagram of an example method of importing data from a contract research organization to a sponsor company's E-Notebook in accordance with an embodiment of the invention.

FIG. 10 is a swim-lane diagram of an example method 1000 of importing data from a contract research organization 202 to a sponsor company's electronic laboratory notebook 218 in accordance with an embodiment of the invention.

In some implementations, the method 1000 includes accessing the E-Notebook data loader 206 (step 902), as described in relation to FIGS. 8 and 9. Similar to the above described export job, the import job may be run immediately, at scheduled intervals, and on demand.

The method 1000 may include adding or configuring an import action, as described in relation to FIGS. 4 and 5A. Once a scheduled import action has been created, updated, or made active, the Data Loader Job Scheduler 416 may initiate an import job once the schedule condition is met.

In some implementations, the E-Notebook data loader 206 may initiate an import job by allowing the administrator preview a list of exportable collection from the local E-Notebook 218 of the contract research organization 202. An administrator may use the graphical user interface 302 to send a preview request for a list of exportable collection to the Data Loader Service 418 (step 1002), which then transmits the request to the Data Loader Staging component 308 and local database 306 of the E-Notebook data loader 206 (step 1004). The Data Loader Staging component 308 and local database 306 returns the list of exportable collection to the Data Loader Service 418 (step 1006), which then transmits the list to the graphical user interface 302 for the administrator to preview (step 1008).

The Data Loader Staging component 308 and local database 306 may return the saved collection being stored at the local database 306 to the Data Loader services 418 (step 1014).

Upon an administrator initiating an import job action at the graphical user interface 302 (step 1014), the Data Loader services 418 may initiate an import collection API of the sponsor company E-Notebook 208 to import the saved collection thereto (step 1016). The Data Loader services 418 may provide the imported collection to the sponsor company E-Notebook 208 (step 1018).

In some implementations, the Data Loader services 418 may update the job status (step 1020) and send the notification of the import (step 1022).

Figure 11:
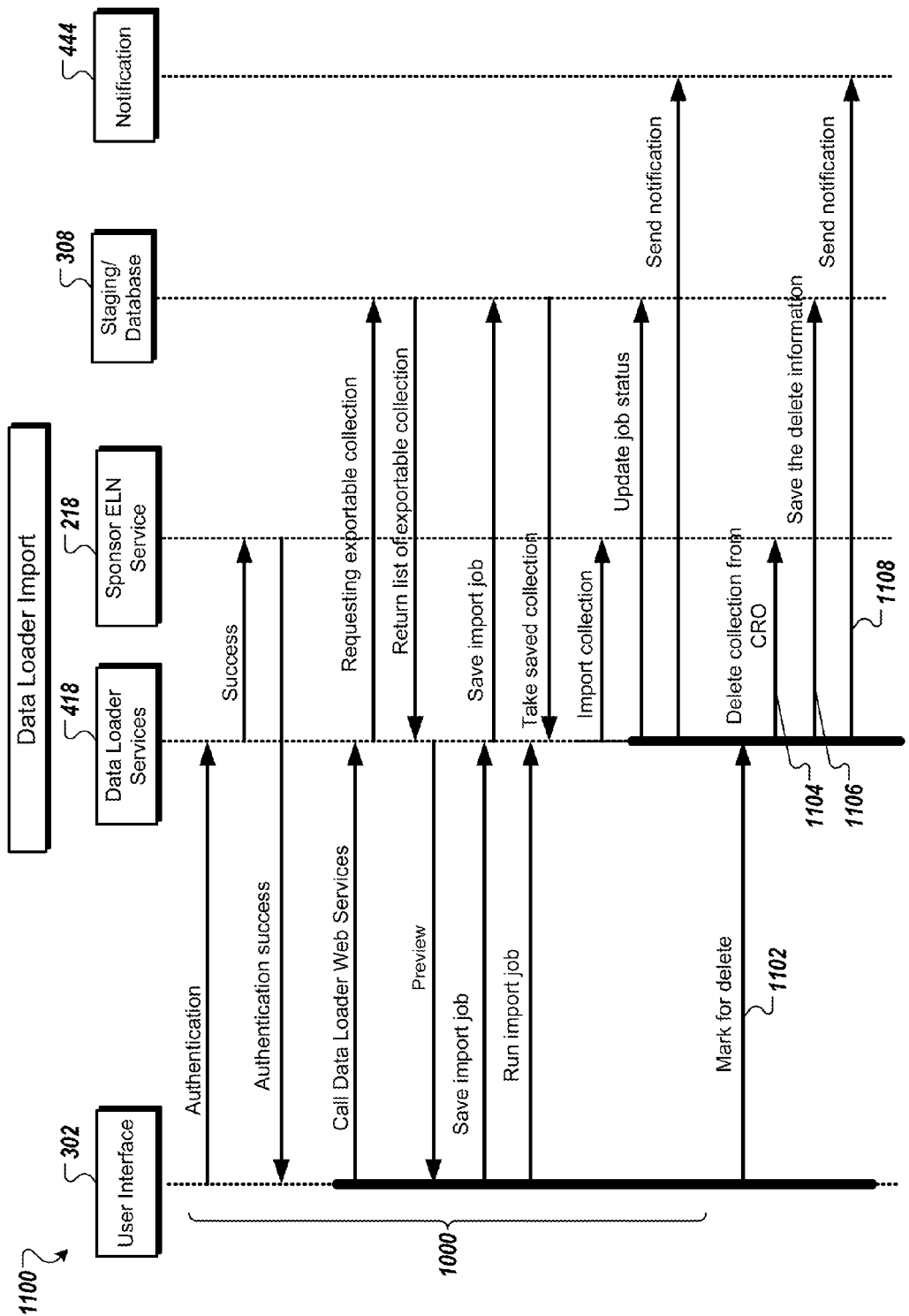
FIG. 11 is a swim-lane diagram of an example method of deleting data between a contract research organization and a sponsor company's E-Notebook in accordance with an embodiment of the invention.

FIG. 11 is a swim-lane diagram of an example method 1100 of deleting data between a contract research organization 202 and a sponsor company's electronic laboratory notebook 218 in accordance with an embodiment of the invention. The E-Notebook data loader 206 may delete a job permanently from local E-Notebook 218 if it is no longer required, and if it has been updated at least once to the sponsor company E-Notebook 208.

In some implementations, the method 1100 may be performed subsequent to an export or import action, as described and shown in relation to FIGS. 10 and 11. Here, relevant portion of the method 1000 of FIG. 10 is reproduced.

In some implementations, the method 1100 may include the administrator designating an export or import action with a delete action when creating or running the respective export/import jobs (step 1102). Subsequent to the import or export job, the Data Loader service 418 may transmit a request to delete the collection from the CRO (step 1104). This request may serve as an acknowledgment to the local E-Notebook 218 that its CRO data has been properly transmitted to the sponsor company E-Notebook 208 or has been stored at the E-Notebook data loader 206.

In some implementations, the Data Loader service 418 may temporary store the deleted information locally in the database 306 (step 1106) and send the notification of the delete action (step 1108).

Figure 12:
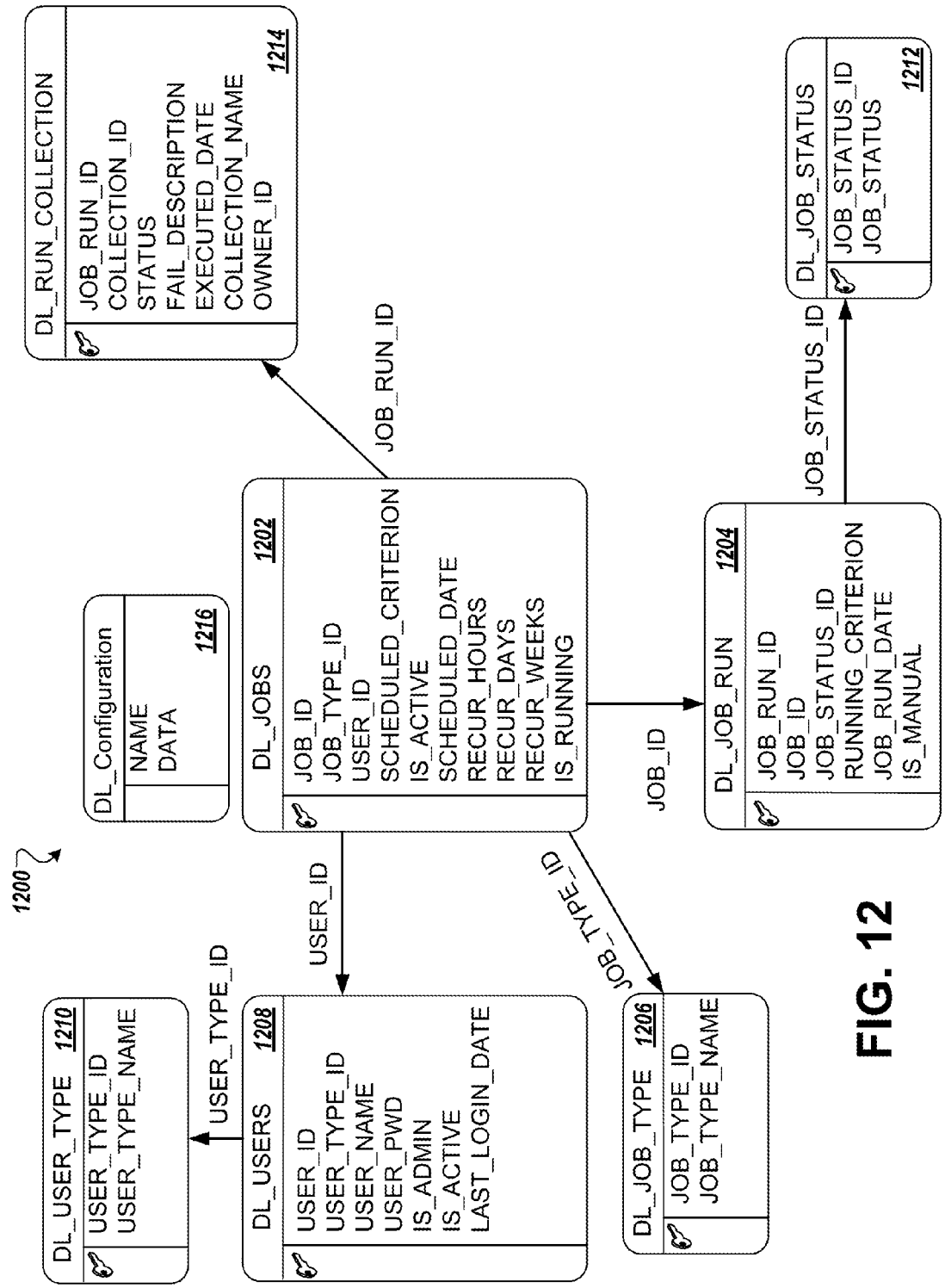
FIG. 12 is an example database utilized by the E-Notebook data loader in accordance with an embodiment of the invention.

FIG. 12 is an example database 1200 utilized by the E-Notebook data loader 206 in accordance with an embodiment of the invention. As shown, the database 1200 includes a jobs table 1202, a job-run table 1204, a job-type table 1206, a user table 1208, a user-type table 1210, a job-status table 1212, a run-collection table 1214, and a configuration table 1216. The database 1200 may be stored within a relational database or document-oriented database. Examples of databases include MySQL, Oracle, SAP, dBASE, HANA, and IBM DB2. In some implementations, the tables may include a primary key for searching.

In some implementations, the jobs table 1202 may include a "job_id" field, "job_type_id" field, a "user_id" field, a "scheduled_criterion" field, an "is_active" field, a "scheduled_date" field, a "recur_hours" field, a "recur_days" field, a "recur_week" field, and a "is_running" field. These data fields may be associated with the information provided by an administrator when scheduling a new job, as described in relation to FIG. 4. The primary key may in the "job_id" field.

In some implementations, the job-run table 1204, the job-type table 1206, and the job-status 1212 may be associated to an action of a given Job runner (430, 432, 434, 436, and 438). The table 1204 may include a "job_run_id" field, a "job_id" field, a "job_status_id" field, a "job_run_date" field, and an "is_manual" field. The table 1206 may include a "job_type_id" field and a "job_type_name" field. The table 1212 may include a "job_status_id" field and a "job_status" field. The primary key may include the "job_run_id" field, the "job_type_id" field, and the "job_status_id" field.

In some implementations, the user table 1208 and the user-type table 1210 are associated with a respective user of the E-notebook data loader 206, including the administrator, the CRO researchers, and the sponsor company's analyst. The table 1208 may include a "user_id" field, a "user_type_id" field, a "user_name" field, a "user_pwd" field, a "is_admin" field, a "is_active" field, and a "last_login_date" field. The table 1210 may include a "user_type_id" field and a "user_type_name" field. The primary key may include the "user_id" field and the "user_type_id" field.

In some implementations, the run-collection table 1214 is associated to a CRO research record or collection thereof. The table 1214 may include a "job_run_id" field, a "collection_id" field, a "status" field, a "fail_description" field, an "executed_date" field, a "collection_name" field, and an "owner_id" field. The primary key may include the "job_run_id" field.

In some implementations, the configuration table 1216 is associated to a version of the E-notebook data loader 206. The table 1216 may include a "name" field and a "data" field.

Figure 13:
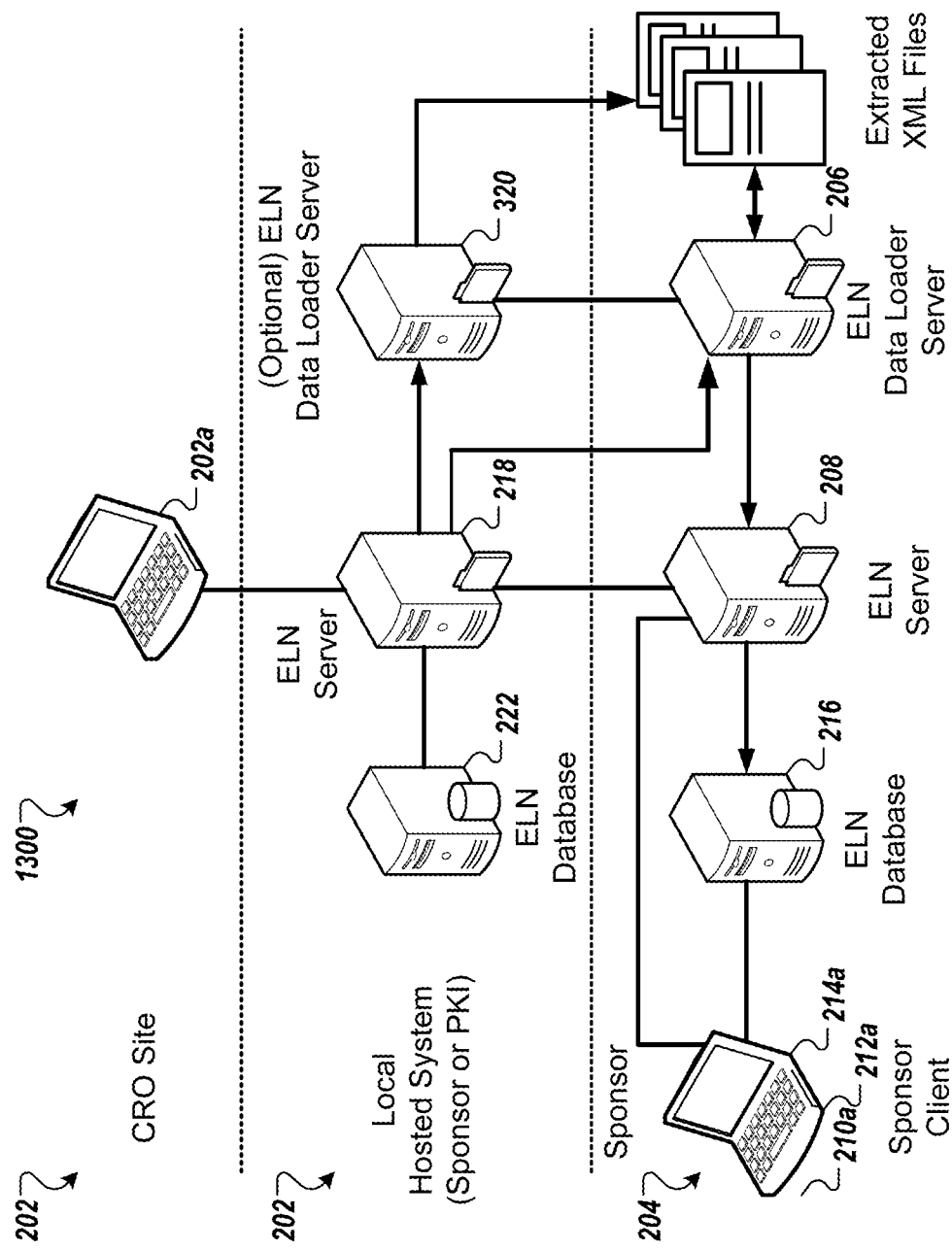
FIG. 13 is a diagram of an example system in accordance with an illustrative embodiment of the invention.

FIG. 13 is a diagram of an example system 1300 in accordance with an illustrative embodiment of the invention. The system 1300 is shown as a "three-tier" workstation. The "three-tier" workstation may be utilized to minimize the number of user licenses. The "3-tier" workstation may also be utilized to minimize the data loading and merging effort, particularly for local E-Notebook 218 located at the same CRO 202 having the same geographic location.

In addition to the E-Notebook data loader 206 (e.g., on site at main corporation), the figure further shows a remote Data Loader servers 320 that can be cloud-based, or located in the entity's (e.g., main corporation's) offshore network, for example. Each of these remote servers may interface with (e.g., collect data from, and/or process data received from) clients of the local E-notebook 218, whom may be located in multiple geographical locations.

Figure 14:
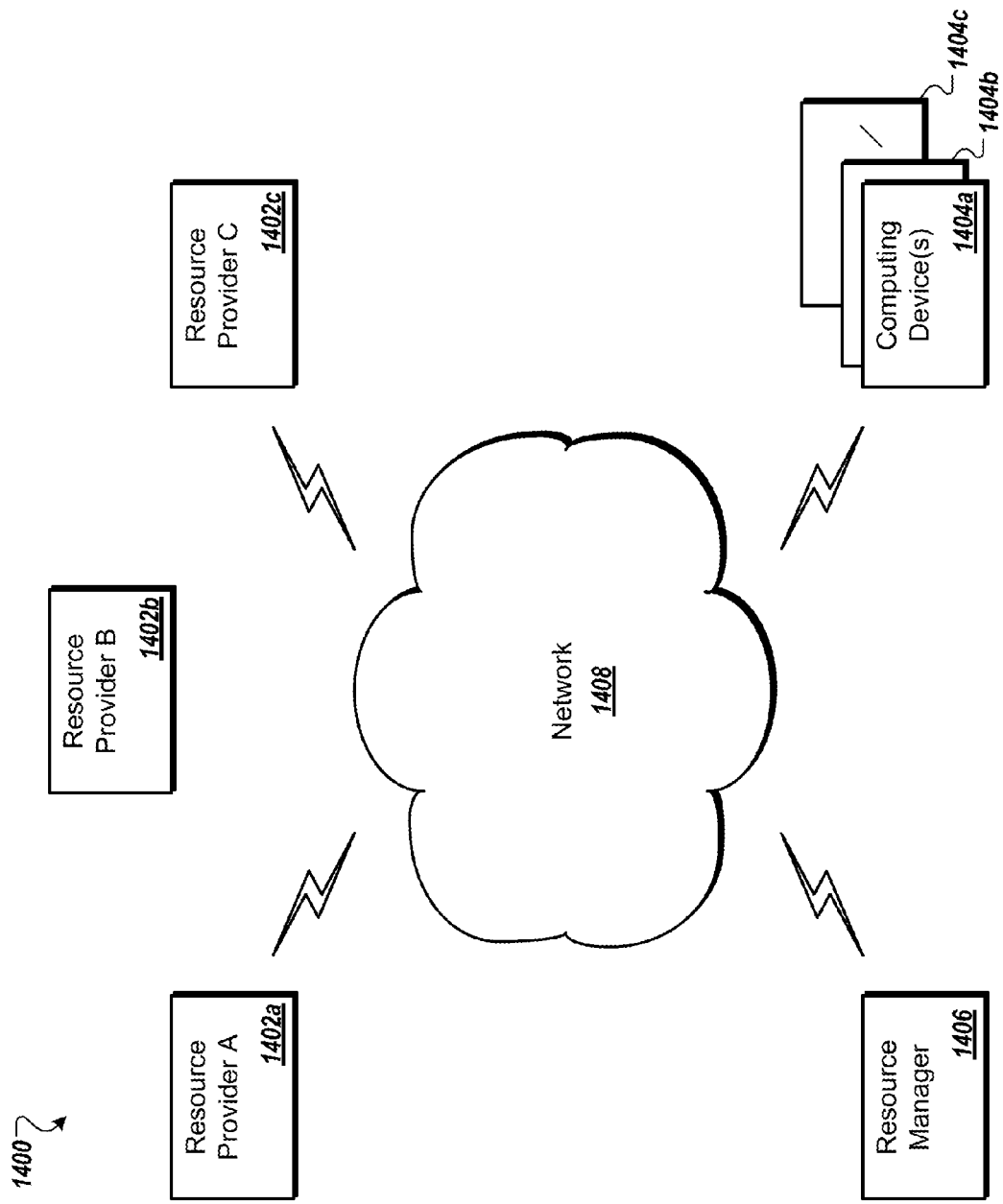
FIG. 14 shows an illustrative network environment for use in the methods and systems for secure upload and management of data from the contract research organization to an entity centralized E-Notebook, described herein

FIG. 14 shows an illustrative network environment 1400 for use in the methods and systems for secure upload and management of data from CROs to an entity centralized ELN described herein. The cloud computing environment 1400 may include one or more resource providers 1402a, 1402b, 1402c (collectively, 1402). Each resource provider 1402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 1402 may be connected to any other resource provider 1402 in the cloud computing environment 1400. In some implementations, the resource providers 1402 may be connected over a computer network 1408. Each resource provider 1402 may be connected to one or more computing device 1404a, 1404b, 1404c (collectively, 1404), over the computer network 1408.

The cloud computing environment 1400 may include a resource manager 1406. The resource manager 1406 may be connected to the resource providers 1402 and the computing devices 1404 over the computer network 1408. In some implementations, the resource manager 1406 may facilitate the provision of computing resources by one or more resource providers 1402 to one or more computing devices 1404. The resource manager 1406 may receive a request for a computing resource from a particular computing device 1404. The resource manager 1406 may identify one or more resource providers 1402 capable of providing the computing resource requested by the computing device 1404. The resource manager 1406 may select a resource provider 1402 to provide the computing resource. The resource manager 1406 may facilitate a connection between the resource provider 1402 and a particular computing device 1404. In some implementations, the resource manager 1406 may establish a connection between a particular resource provider 1402 and a particular computing device 1404. In some implementations, the resource manager 1406 may redirect a particular computing device 1404 to a particular resource provider 1402 with the requested computing resource.

Figure 15:
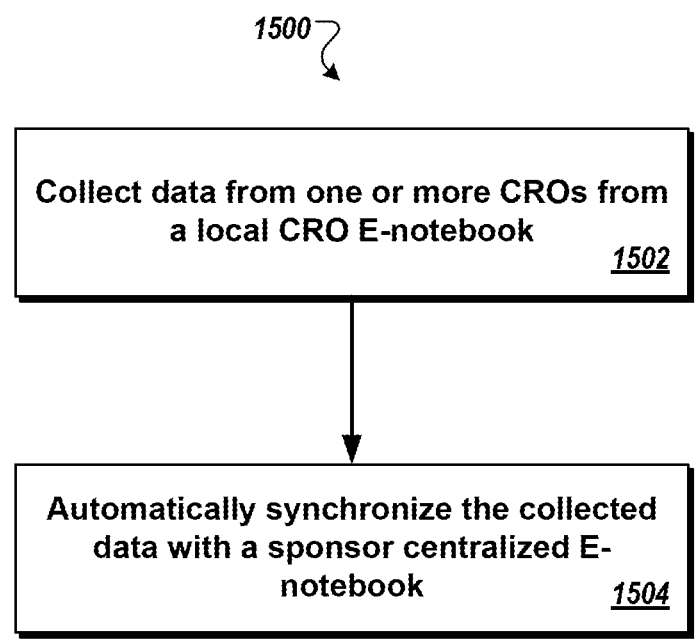
FIG. 15 is a flowchart of an example method of secure upload and management of data from one or more contract research organizations to an entity's centralized E-Notebook in accordance with an embodiment of the invention.

FIG. 15 is a flowchart of an example method 1500 of secure upload and management of data from one or more contract research organizations 202 to an entity's centralized E-Notebook 208 in accordance with an embodiment of the invention. The method 1500 may include collecting, by an entity computing device, over a network, data from one or more contract research organizations 202 where the data may be collected from the local electronic notebooks 218 (step 1502). Each of the local electronic notebooks 218 may have the same configuration as the centralized electronic laboratory notebook 208. The content of each of the local electronic notebooks 218 may be limited to contents specific to the respective contract research organization 202. The collection of data may be performed at the site of the contract research organization 202. The collection of data may be performed at an external server. The collection may be performed a scheduled manner without any interaction by an end-user after the schedule is configured. The collection may be performed over a VPN connection. The collection may be performed over a SSL connection. The collection may be performed across a firewall.

In some implementations, the method 1500 may include automatically synchronizing (step 1504), by the entity computing device, the data collected from the contract research organizations 202 with data contained in the centralized electronic laboratory notebook 208. In some implementations, the method may further include causing, by the entity computing device, a notification to be sent upon a successful update of the collection of the CRO data, an update, a modification, a delete action, or a failed action.

It is contemplated that systems, devices, methods, and processes of the claimed invention encompass variations and adaptations developed using information from the embodiments described herein. Adaptation and/or modification of the systems, devices, methods, and processes described herein may be performed by those of ordinary skill in the relevant art.

Figure 16:
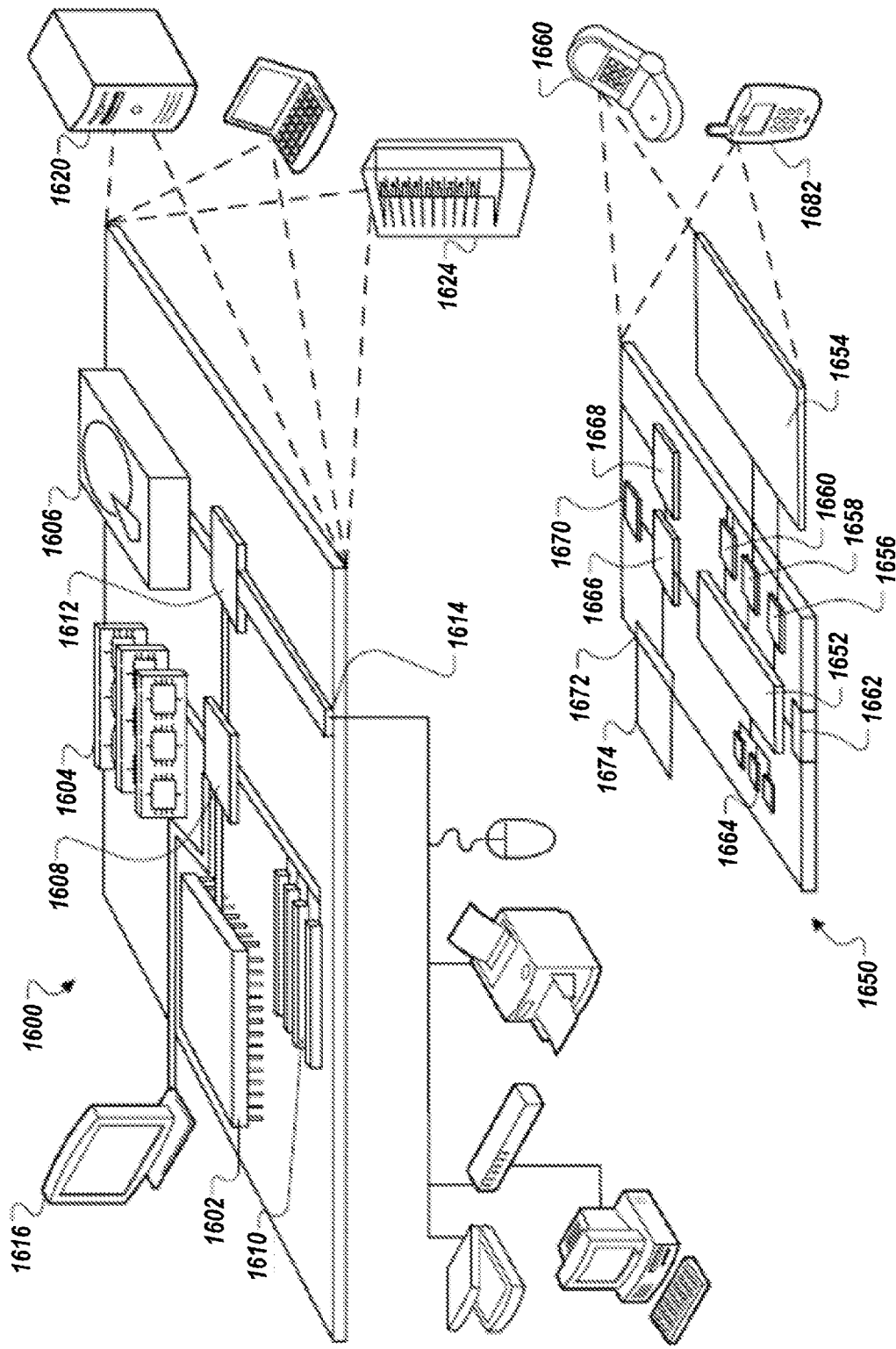
FIG. 16 shows an example of a computing device and a mobile computing device that can be used in the methods and systems described in this disclosure.

FIG. 16 shows an example of a computing device 1600 and a mobile computing device 1650 that can be used in the methods and systems described in this disclosure. The computing device 1600 is intended to represent various forms of digital computers, such as laptops, desktops, workstations, personal digital assistants, servers, blade servers, mainframes, and other appropriate computers. The mobile computing device 1650 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 1600 includes a processor 1602, a memory 1604, a storage device 1606, a high-speed interface 1608 connecting to the memory 1604 and multiple high-speed expansion ports 1610, and a low-speed interface 1612 connecting to a low-speed expansion port 1614 and the storage device 1606. Each of the processor 1602, the memory 1604, the storage device 1606, the high-speed interface 1608, the high-speed expansion ports 1610, and the low-speed interface 1612, are interconnected using various busses, and may be mounted on a common motherboard or in other manners as appropriate. The processor 1602 can process instructions for execution within the computing device 1600, including instructions stored in the memory 1604 or on the storage device 1606 to display graphical information for a GUI on an external input/output device, such as a display 1616 coupled to the high-speed interface 1608. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 1604 stores information within the computing device 1600. In some implementations, the memory 1604 is a volatile memory unit or units. In some implementations, the memory 1604 is a non-volatile memory unit or units. The memory 1604 may also be another form of computer-readable medium, such as a magnetic or optical disk.

The storage device 1606 is capable of providing mass storage for the computing device 1600. In some implementations, the storage device 1606 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 1602), perform one or more methods, such as those described above. The instructions can also be stored by one or more storage devices such as computer- or machine-readable mediums (for example, the memory 1604, the storage device 1606, or memory on the processor 1602).

The high-speed interface 1608 manages bandwidth-intensive operations for the computing device 1600, while the low-speed interface 1612 manages lower bandwidth-intensive operations. Such allocation of functions is an example only. In some implementations, the high-speed interface 1608 is coupled to the memory 1604, the display 1616 (e.g., through a graphics processor or accelerator), and to the high-speed expansion ports 1610, which may accept various expansion cards (not shown). In the implementation, the low-speed interface 1612 is coupled to the storage device 1606 and the low-speed expansion port 1614. The low-speed expansion port 1614, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 1600 may be implemented in a number of different forms, as shown in the figure. For example, it may be implemented as a standard server 1620, or multiple times in a group of such servers. In addition, it may be implemented in a personal computer such as a laptop computer 1622. It may also be implemented as part of a rack server system 1624. Alternatively, components from the computing device 1600 may be combined with other components in a mobile device (not shown), such as a mobile computing device 1650. Each of such devices may contain one or more of the computing device 1600 and the mobile computing device 1650, and an entire system may be made up of multiple computing devices communicating with each other.

The mobile computing device 1650 includes a processor 1652, a memory 1664, an input/output device such as a display 1654, a communication interface 1666, and a transceiver 1668, among other components. The mobile computing device 1650 may also be provided with a storage device, such as a micro-drive or other device, to provide additional storage. Each of the processor 1652, the memory 1664, the display 1654, the communication interface 1666, and the transceiver 1668, are interconnected using various buses, and several of the components may be mounted on a common motherboard or in other manners as appropriate.

The processor 1652 can execute instructions within the mobile computing device 1650, including instructions stored in the memory 1664. The processor 1652 may be implemented as a chipset of chips that include separate and multiple analog and digital processors. The processor 1652 may provide, for example, for coordination of the other components of the mobile computing device 1650, such as control of user interfaces, applications run by the mobile computing device 1650, and wireless communication by the mobile computing device 1650.

The processor 1652 may communicate with a user through a control interface 1658 and a display interface 1656 coupled to the display 1654. The display 1654 may be, for example, a TFT (Thin-Film-Transistor Liquid Crystal Display) display or an OLED (Organic Light Emitting Diode) display, or other appropriate display technology. The display interface 1656 may comprise appropriate circuitry for driving the display 1654 to present graphical and other information to a user. The control interface 1658 may receive commands from a user and convert them for submission to the processor 1652. In addition, an external interface 1662 may provide communication with the processor 1652, so as to enable near area communication of the mobile computing device 1650 with other devices. The external interface 1662 may provide, for example, for wired communication in some implementations, or for wireless communication in other implementations, and multiple interfaces may also be used.

The memory 1664 stores information within the mobile computing device 1650. The memory 1664 can be implemented as one or more of a computer-readable medium or media, a volatile memory unit or units, or a non-volatile memory unit or units. An expansion memory 1674 may also be provided and connected to the mobile computing device 1650 through an expansion interface 1672, which may include, for example, a SIMM (Single In Line Memory Module) card interface. The expansion memory 1674 may provide extra storage space for the mobile computing device 1650, or may also store applications or other information for the mobile computing device 1650. Specifically, the expansion memory 1674 may include instructions to carry out or supplement the processes described above, and may include secure information also. Thus, for example, the expansion memory 1674 may be provided as a security module for the mobile computing device 1650, and may be programmed with instructions that permit secure use of the mobile computing device 1650. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier and, when executed by one or more processing devices (for example, processor 1652), perform one or more methods, such as those described above. The instructions can also be stored by one or more storage devices, such as one or more computer- or machine-readable mediums (for example, the memory 1664, the expansion memory 1674, or memory on the processor 1652). In some implementations, the instructions can be received in a propagated signal, for example, over the transceiver 1668 or the external interface 1662.

The mobile computing device 1650 may communicate wirelessly through the communication interface 1666, which may include digital signal processing circuitry where necessary. The communication interface 1666 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 1668 using a radio-frequency. In addition, short-range communication may occur, such as using a Bluetooth®, Wi-Fi™, or other such transceiver (not shown). In addition, a GPS (Global Positioning System) receiver module 1670 may provide additional navigation- and location-related wireless data to the mobile computing device 1650, which may be used as appropriate by applications running on the mobile computing device 1650.

The mobile computing device 1650 may also communicate audibly using an audio codec 1660, which may receive spoken information from a user and convert it to usable digital information. The audio codec 1660 may likewise generate audible sound for a user, such as through a speaker, e.g., in a handset of the mobile computing device 1650. Such sound may include sound from voice telephone calls, may include recorded sound (e.g., voice messages, music files, etc.) and may also include sound generated by applications operating on the mobile computing device 1650.

The mobile computing device 1650 may be implemented in a number of different forms, as shown in the figure. For example, it may be implemented as a cellular telephone 1680. It may also be implemented as part of a smart-phone 1682, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While the invention has been particularly shown and described with reference to specific preferred embodiments, it should be understood by those skilled in the art that various changes in form and detail may be made therein without departing from the spirit and scope of the invention as defined by the appended claims.

Throughout the description, where articles, devices, and systems are described as having, including, or comprising specific components, or where processes and methods are described as having, including, or comprising specific steps, it is contemplated that, additionally, there are articles, devices, and systems of the present invention that consist essentially of, or consist of, the recited components, and that there are processes and methods according to the present invention that consist essentially of, or consist of, the recited processing steps.

What is claimed is:

1. A method for secure upload and management of data from a plurality of contract research organizations to a centralized electronic laboratory notebook of a sponsor company, the method comprising:
    collecting, by a data loader of a sponsor company computing device, over a network, data from the plurality of contract research organizations for storage in the centralized electronic laboratory notebook of the sponsor company, wherein
        the data loader of the sponsor company comprises a data loader staging component to temporarily store the data from the plurality of contract research organizations, a back-end service to organize the data temporarily stored in the data loader staging component, a graphical user interface that allows an end-user to configure the back-end service, and a download database to permanently store the data temporarily stored in the data loader staging component and
        the data is collected from local electronic notebooks, each corresponding to a respective contract research organization, wherein
            (i) the content of each of the local electronic notebooks is limited to content specific to the respective contract research organization,
            (ii) each of the respective contract research organizations is prevented from accessing the centralized electronic laboratory notebook of the sponsor company, and
            (iii) each of the local electronic notebooks comprises a server component, a local database, and a client component, wherein
                the client component is a front end application with which multiple users at the respective contract research organization interface in order to record the data, and
                data from the local database is of the same format as data in the centralized electronic laboratory notebook of the sponsor company or is converted by the data loader to a common format; and
    automatically synchronizing, by the data loader of the sponsor company computing device, the data collected from the plurality of contract research organizations with data contained in the centralized electronic laboratory notebook of the sponsor company, wherein:
        each of the plurality of contract research organizations is an organization that provides support to the sponsor company in the form of research services outsourced by the sponsor company on a contract basis,
        the sponsor company is a corporate sponsor company in one or more industries selected from the group consisting of pharmaceutical, biotechnology, and medical device industries, and
        each of the local electronic notebooks comprises a computing application to document research, experiments and procedures performed in a laboratory.

2. The method of claim 1, wherein the collecting of the data is performed on-premises of the contract research organization.

3. The method of claim 1, wherein the collecting of the data is performed at an external server.

4. The method of claim 1, wherein the collecting is performed in a scheduled manner without any interaction by an end-user of the sponsor company after the schedule is configured.

5. The method of claim 1, wherein the collecting is performed over a virtual private network (VPN) connection.

6. The method of claim 1, wherein the collecting is performed over a Secure Sockets Layer (SSL) connection.

7. The method of claim 1, wherein the collecting is performed across a firewall.

8. The method of claim 1 further comprising:
    causing, by the sponsor company computing device, a notification to be sent upon at least one condition selected from a group consisting of a successful update of the collecting of the data, a failed update, a modification, or a creation of a new collection.

9. The method of claim 1, wherein at least a portion of the data collected from the plurality of contract research organizations by the sponsor company computing device is first collected by a remote sponsor company server prior to the collecting by the sponsor company computing device and the synchronizing by the sponsor company computing device with the centralized electronic laboratory notebook data.

10. The method of claim 1, wherein the plurality of contract research organizations includes at least two organization located at different sites.

11. A system for secure upload and management of data from a plurality of contract research organizations to a centralized electronic laboratory notebook of a sponsor company, the system comprising:
    a processor of a sponsor company computing device; and
    a memory, the memory storing instructions that, when executed by the processor, cause the processor to:
        collect, by a data loader of the sponsor company computing device, over a network, data from the plurality of contract research organizations for storage in the centralized electronic laboratory notebook of the sponsor company, wherein
the data loader of the sponsor company comprises a data loader staging component to temporarily store the data from the plurality of contract research organizations, a back-end service to organize the data temporarily stored in the data loader staging component, a graphical user interface that allows an end-user to configure the back-end service, and a download database to permanently store the data temporarily stored in the data loader staging component; and
the data is collected from local electronic notebooks, each corresponding to a respective contract research organization, wherein
(i) the content of each of the local electronic notebooks is limited to content specific to the respective contract research organization,
(ii) each of the respective contract research organizations is prevented from accessing the centralized electronic laboratory notebook of the sponsor company, and
(iii) each of the local electronic notebooks comprises a server component, a local database, and a client component, wherein
the client component is a front end application with which multiple users at the respective contract research organization interface in order to record the data, and
data from the local database is of the same format as data in the centralized electronic laboratory notebook or is converted by the data loader to a common format; and
automatically synchronize the data collected from the plurality of contract research organizations with data contained in the centralized electronic laboratory notebook of the sponsor company, wherein:
each of the plurality of contract research organizations is an organization that provides support to the sponsor company in the form of research services outsourced by the sponsor company on a contract basis,
the sponsor company is a corporate sponsor company in one or more industries selected from the group consisting of pharmaceutical, biotechnology, and medical device industries, and
each of the local electronic notebooks comprises a computing application to document research, experiments and procedures performed in a laboratory.

12. A non-transitory computer readable medium having instructions stored thereon, wherein the instructions, when executed by a processor of a sponsor company computing device, cause the processor to:
collect, by a data loader of the sponsor company computing device, over a network, data from a plurality of contract research organizations for storage in a centralized electronic laboratory notebook of the sponsor company, wherein
the data loader of the sponsor company comprises a data loader staging component to temporarily store the data from the plurality of contract research organizations, a back-end service to organize the data temporarily stored in the data loader staging component, a graphical user interface that allows an end-user to configure the back-end service, and a download database to permanently store the data temporarily stored in the data loader staging component; and the data is collected from local electronic notebooks, each corresponding to a respective contract research organization, wherein
(i) the content of each of the local electronic notebooks is limited to content specific to the respective contract research organization,
(ii) each of the respective contract research organizations is prevented from accessing the centralized electronic laboratory notebook of the sponsor company, and
(iii) each of the local electronic notebooks comprises a server component, a local database, and a client component, wherein
the client component is a front end application with which multiple users at the respective contract research organization interface in order to record the data, and
data from the local database is of the same format as data in the centralized electronic laboratory notebook or is converted by the data loader to a common format; and
automatically synchronize the data collected from the plurality of contract research organizations with data contained in the centralized electronic laboratory notebook of the sponsor company, wherein:
each of the plurality of contract research organizations is an organization that provides support to the sponsor company in the form of research services outsourced by the sponsor company on a contract basis,
the sponsor company is a corporate sponsor company in one or more industries selected from the group consisting of pharmaceutical, biotechnology, and medical device industries, and
each of the local electronic notebooks comprises a computing application to document research, experiments and procedures performed in a laboratory.

13. A method for secure upload and management of data from a plurality of contract research organizations to a centralized electronic laboratory notebook of a sponsor company, the method comprising:
scheduling, by a sponsor company computing device, a transfer of data collected from the plurality of contract research organizations to the centralized electronic laboratory notebook of the sponsor company, wherein
the data is collected from local electronic notebooks, each corresponding to a respective contract research organization, wherein
(i) the content of each of the local electronic notebooks is limited to content specific to the respective contract research organization,
(ii) each of the respective contract research organizations is prevented from accessing the centralized electronic laboratory notebook of the sponsor company, and
(iii) each of the local electronic notebooks comprises a server component, a local database, and a client component, wherein
the client component is a front end application with which multiple users at the respective contract research organization interface in order to record the data; and
automatically deleting from each local electronic notebook, by the sponsor company computing device, the data collected from the plurality of contract research organizations after the transfer, wherein:
each of the plurality of contract research organizations is an organization that provides support to the sponsor company in the form of research services outsourced by the sponsor company on a contract basis, the sponsor company is a corporate sponsor company in one or more industries selected from the group consisting of pharmaceutical, biotechnology, and medical device industries, and each of the local electronic notebooks comprises a computing application to document research, experiments and procedures performed in a laboratory.

14. The method of claim 13, wherein data from each local database is of the same format as data in the centralized electronic laboratory notebook or is converted by a data loader of the sponsor company computing device to a common format.

15. The method of claim 13, wherein the scheduling includes an exporting action of the data.

16. The method of claim 13, wherein the scheduling includes an importing action of the data.

17. The method of claim 13, wherein the scheduling includes a deleting action of the data.

18. The method of claim 13, wherein the scheduling is configured over a Web interface.

19. The method of claim 13, wherein the scheduling further includes identifying a type of the data for the transfer.

20. A non-transitory computer readable medium having instructions stored thereon, wherein the instructions, when executed by a processor of a sponsor company computing device, cause the processor to:

schedule, by the sponsor company computing device, a transfer of data collected from a plurality of contract research organizations to a centralized electronic laboratory notebook of the sponsor company, wherein the data is collected from local electronic notebooks each corresponding to a respective contract research organization, wherein (i) the content of each of the local electronic notebooks is limited to content specific to the respective contract research organization, (ii) each of the respective contract research organizations is prevented from accessing the centralized electronic laboratory notebook of the sponsor company, and (iii) each of the local electronic notebooks comprises a server component, a local database, and a client component, wherein the client component is a front end application with which multiple users at the respective contract research organization interface in order to record the data; and automatically delete from each local electronic notebook, by the sponsor company computing device, the data collected from the plurality of contract research organizations after the transfer, wherein:

each of the plurality of contract research organizations is an organization that provides support to the sponsor company in the form of research services outsourced by the sponsor company on a contract basis, the sponsor company is a corporate sponsor company in one or more industries selected from the group consisting of pharmaceutical, biotechnology, and medical device industries, and each of the local electronic notebooks comprises a computing application to document research, experiments and procedures performed in a laboratory.

21. A system for secure upload and management of data from a plurality of contract research organizations to a centralized electronic laboratory notebook of a sponsor company, the system comprising:

a processor of a sponsor company computing device; and a memory, the memory storing instructions that, when executed by the processor, cause the processor to:

schedule, by the sponsor company computing device, a transfer of data collected from the plurality of contract research organizations to the centralized electronic laboratory notebook of the sponsor company, wherein the data is collected from local electronic notebooks each corresponding to a respective contract research organization, wherein (i) the content of each of the local electronic notebooks is limited to content specific to the respective contract research organization, (ii) each of the respective contract research organizations is prevented from accessing the sponsor company's centralized electronic laboratory notebook, and (iii) each of the local electronic notebooks comprises a server component, a local database, and a client component, wherein the client component is a front end application with which multiple users at the respective contract research organization interface in order to record the data; and automatically delete from each local electronic notebook, by the sponsor company computing device, the data collected from the plurality of contract research organizations after the transfer, wherein:

each of the plurality of contract research organizations is an organization that provides support to the sponsor company in the form of research services outsourced by the sponsor company on a contract basis, the sponsor company is a corporate sponsor company in one or more industries selected from the group consisting of pharmaceutical, biotechnology, and medical device industries, and each of the local electronic notebooks comprises a computing application to document research, experiments and procedures performed in a laboratory.

* * * * *